(12) United States Patent
Baba et al.

(10) Patent No.: US 8,721,548 B2
(45) Date of Patent: May 13, 2014

(54) ULTRASONIC DIAGNOSIS APPARATUS, AUTOMATIC SUPPORT APPARATUS, AND AUTOMATIC SUPPORT METHOD

(75) Inventors: Tatsuro Baba, Otawara (JP); Naohisa Kamiyama, Otawara (JP); Shuichi Kawasaki, Nasushiobara (JP); Cong Yao, Otawara (JP); Kenji Hamada, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 517 days.

(21) Appl. No.: 12/822,618

(22) Filed: Jun. 24, 2010

(65) Prior Publication Data
US 2010/0331700 A1    Dec. 30, 2010

(30) Foreign Application Priority Data
Jun. 26, 2009    (JP) .................................. 2009-152336

(51) Int. Cl.
*A61B 8/00*    (2006.01)

(52) U.S. Cl.
USPC ........... 600/454; 600/407; 600/437; 600/441; 600/450; 600/509

(58) Field of Classification Search
USPC ............. 600/407, 437, 441, 454, 509; 607/45
See application file for complete search history.

(56) References Cited

U.S. PATENT DOCUMENTS

| | | | |
|---|---|---|---|
| 5,156,154 A * | 10/1992 | Valenta et al. ................. | 600/455 |
| 5,742,522 A * | 4/1998 | Yazici et al. .................. | 702/185 |
| 6,117,601 A * | 9/2000 | Kanazawa et al. .............. | 430/30 |
| 7,513,872 B2 | 4/2009 | Baba et al. | |
| 7,801,591 B1 * | 9/2010 | Shusterman .................. | 600/509 |
| 2004/0204868 A1* | 10/2004 | Maynard et al. ................ | 702/30 |
| 2006/0265022 A1* | 11/2006 | John et al. ....................... | 607/45 |

FOREIGN PATENT DOCUMENTS

| | | |
|---|---|---|
| JP | 2003-61964 | 3/2003 |
| JP | 2006-149679 | 6/2006 |
| JP | 2007-21212 | 2/2007 |

(Continued)

OTHER PUBLICATIONS

Hiroki Matsui, et al., "Assessment of a Training Protocol of Echocardiographic Examination: Accuracy and Reproducibility", J Med Ultrasonics, vol. 29, No. 6, 2002, pp. 537-544. (with English Abstract).

(Continued)

*Primary Examiner* — Baisakhi Roy
(74) *Attorney, Agent, or Firm* — Oblon, Spivak, McClelland, Maier & Neustadt, L.L.P.

(57) ABSTRACT

According to one embodiment, an ultrasonic diagnosis apparatus includes a storage unit, a ultrasonic probe, a transmission/reception unit, a measured value calculation unit, a distance calculation unit, and a determination unit. The storage unit stores data of a state space based on a first measured values of a measurement item associated with an able-bodied person. The transmission/reception unit transmits ultrasonic waves to a subject via an ultrasonic probe, and generates reception signals corresponding to an ultrasonic waves reflected by the subject. The measured value calculation unit calculates a second measured value of the measurement item associated with the subject based on the reception signals. The distance calculation unit calculates a Mahalanobis distance of the subject based on the state space and the second measured value. The determination unit compares the Mahalanobis distance with a threshold to determine whether the subject has the disease evaluated by the measurement item.

15 Claims, 13 Drawing Sheets

(56) References Cited

FOREIGN PATENT DOCUMENTS

| JP | 2007-531602 | 11/2007 |
|---|---|---|
| JP | 2008-284263 | 11/2008 |
| JP | 2009-22364 | 2/2009 |
| WO | WO 2010/064663 A1 | 6/2010 |

OTHER PUBLICATIONS

Katsusuke Kajihara. et al., "Questionnaire Survey on the State of Routine Echocardiographic Examinations in Japan : Second Report", J Med Ultrasonics, vol. 32, No. 3, 2005, pp. 329-337. (with English Abstract).

Sachiko Watanabe, et al., "Influence of Aging on Cardiac Function Examined by Echocardiography", J Med Ultrasonics, vol. 29, No. 2, 2002, pp. 145-151. (with English Abstract).

Hisato Nakajima, et al., "The Examination of New Standard for Liver Transplantation Adaptation using the Mahalanobis-Taguchi System", Quality Engineering, vol. 14, No. 4, Aug. 2006, pp. 550-558 (with English Abstract).

Tatsuji Kanetaka, et al., "MT System and Dagnosis of Liver Disease (2)", Quality Engineering, vol. 15, No. 4, Aug. 2007, pp. 52-57. (with English Abstract).

Taro Tetsumi, et al., "Estimation of Optimal Settings by MT Method", Quality Engineering, vol. 16, No. 3, Jun. 2008, pp. 93-100. (with English Abstract).

U.S. Appl. No. 12/824,696, filed Jun. 28, 2010, Baba.

Office Action mailed Jul. 23, 2013, in Japanese Patent Application No. 2009-152336 (with English-language Translation).

Hiroki Matsui, et al. Assessment of a Training Protocol of Echocardiographic Examination: Accuracy and Reproducibility, Ultrasonic Medicine, the Society of Ultrasonic Medicine, Japan, vol. 29, No. 6 (2002), p. J537-J544.

Katsusuke Kajiwara et al. Questionnaire Survey on the State Routine Echocardiographic Examination in Japan: Present Routine Examination of Cardiac Echo Diagrams in Japan ($2_{nd}$ Report on Questionnaires), Ultrasonic Medicine, the Society of Ultrasonic Medicine, Japan, vol. 32, No. 3 (2005), p. 329-337.

Sachiko Watanabe et al., Influence of Aging on Cardiac Function Examined by Echocardiography, Ultrasonic Medicine, Japan, vol. 29, No. 2 (2002), p. J145-J151.

\* cited by examiner

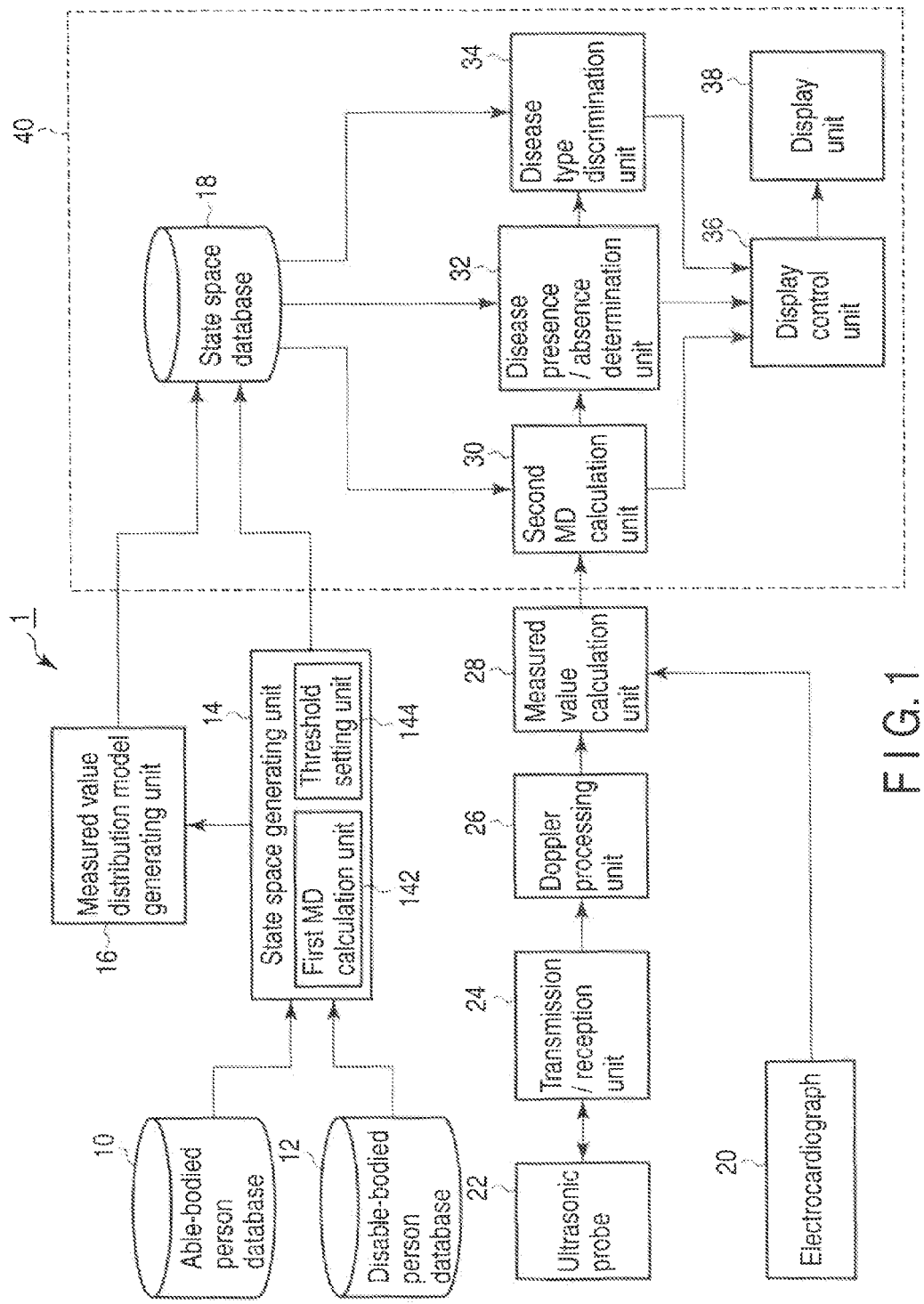
F I G. 1

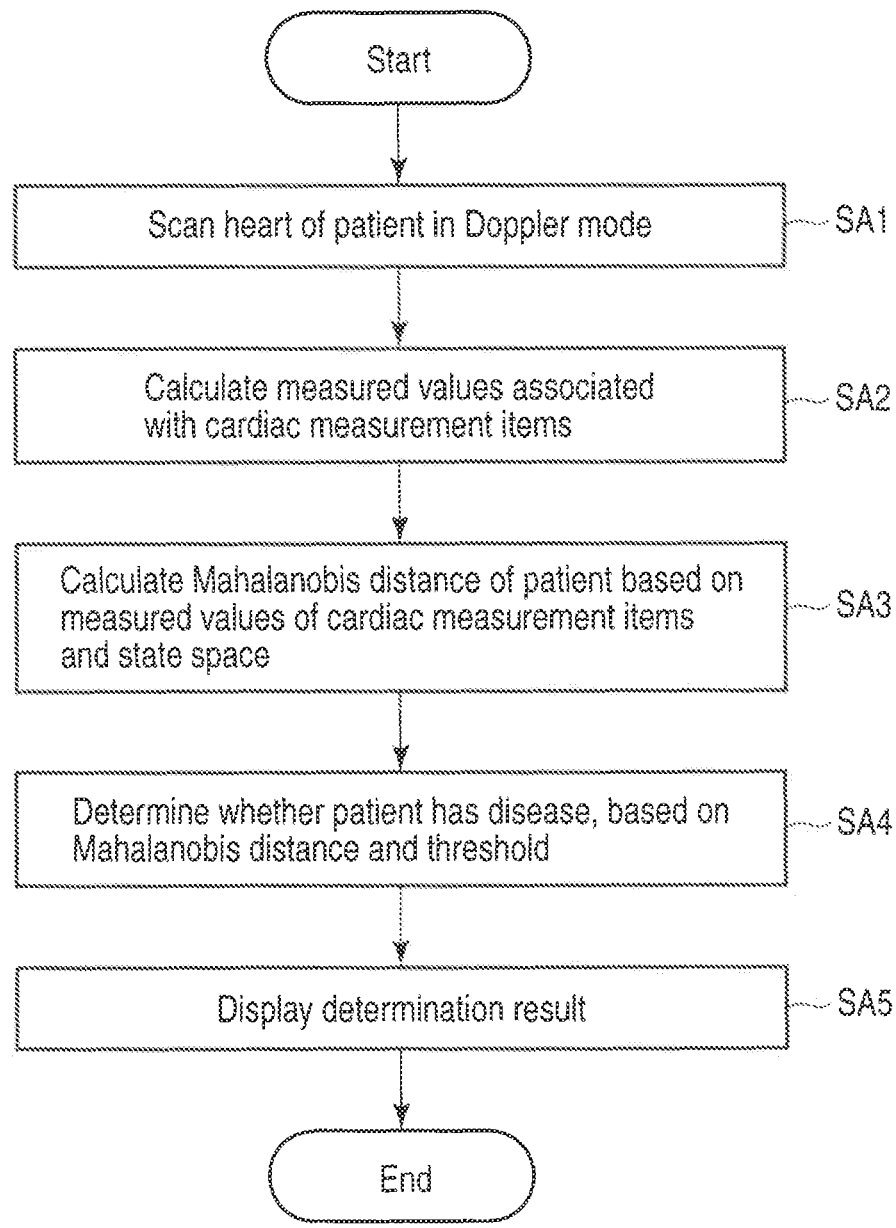
F I G. 2

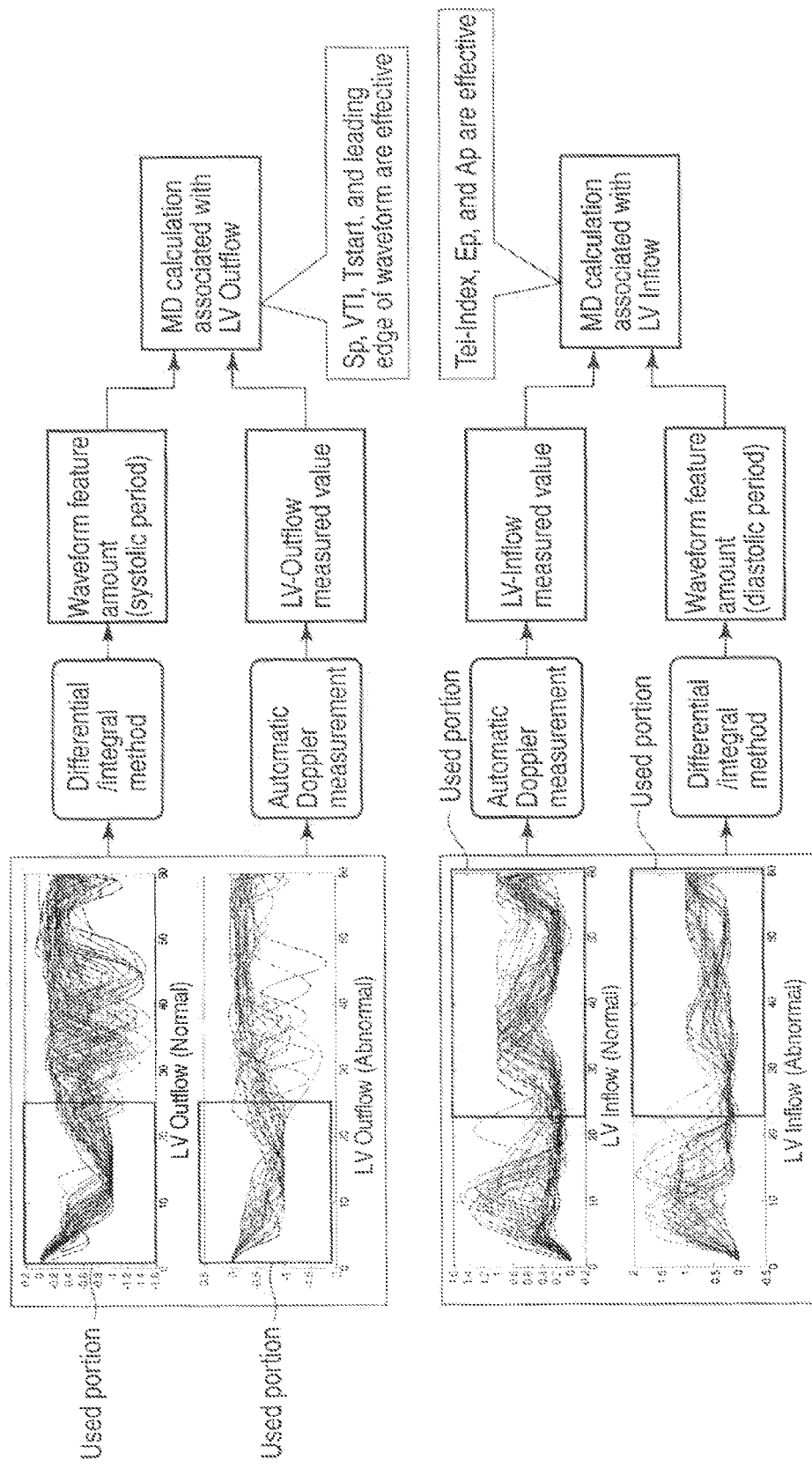
F I G. 5

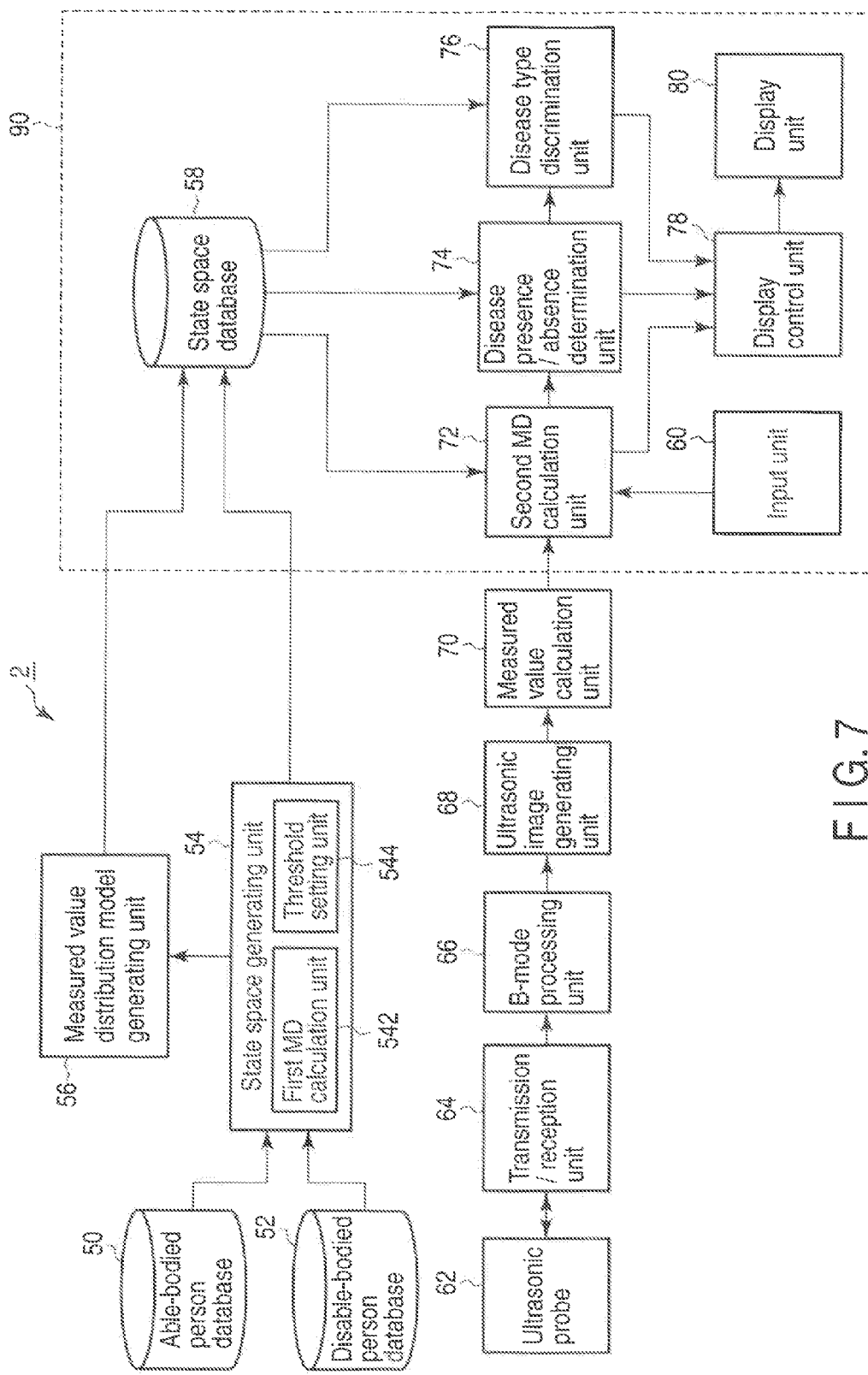
F I G. 7

| No | Edge | Surface | Parenchymal | Splenomegaly | Deformity | Subcutaneous fat [mm] | Diagnosis value |
|---|---|---|---|---|---|---|---|
| 1 | 1 | 0 | 1 | 0 | 0 | 14 | 7.7 |
| 2 | 1 | 0 | 1 | 0 | 1 | 9.5 | 4.1 |
| 3 | 0 | 0 | 0 | 1 | 0 | 11.2 | 7.6 |
| 4 | 1 | 0 | 0 | 0 | 0 | 10.1 | 4.2 |
| 5 | 2 | 2 | 2 | 1 | 2 | 14.3 | 14.4 |
| 6 | 1 | 0 | 0 | 0 | 0 | 13.4 | 4.9 |
| 7 | 0 | 0 | 0 | 0 | 0 | | 5.7 |
| 8 | 2 | 0 | 0 | 0 | 1 | 12.5 | 12.2 |
| 9 | 1 | 0 | 0 | 1 | 1 | 14.3 | 4.6 |
| 85 | 2 | 2 | 2 | 0 | 1 | 14.3 | 11.8 |
| 86 | 0 | 0 | 0 | 0 | 0 | 11.9 | 5 |
| 87 | 2 | 0 | 1 | 0 | 1 | 11.6 | 17.6 |
| 88 | 0 | 0 | 0 | 0 | 0 | 19.8 | 2.7 |
| 89 | 2 | 1 | 1 | 2 | 1 | 15.4 | 48.3 |
| 90 | 2 | 2 | 2 | 0 | 1 | 11.9 | 27.4 |
| 91 | 0 | 0 | 0 | 0 | 0 | 11.2 | 3.8 |
| 92 | 0 | 0 | 0 | 0 | 0 | 13.2 | 4.5 |
| 93 | | | | | | 18.2 | 14.9 |
| 94 | | | | | | 16.7 | 16.7 |
| 95 | 1 | 0 | 0 | 0 | 0 | 17.1 | 10.2 |

FIG. 10

| Able-bodied persons | | | | Disable-bodied persons | | | |
|---|---|---|---|---|---|---|---|
| ID | Label | Distance | OK/NG | ID | Label | Distance | OK/NG |
| 53 | No.070 | 3.59 | NG | 13 | No.042 | 10.173 | NG |
| 44 | No.027 | 3.31 | NG | 32 | No.051 | 9.773 | NG |
| 3 | No.038 | 2.94 | NG | 34 | No.083 | 9.284 | NG |
| 51 | No.040 | 2.49 | NG | 22 | No.017 | 9.217 | NG |
| 43 | No.080 | 2.03 | NG | 29 | No.082 | 7.810 | NG |
| 56 | No.065 | 1.98 | NG | 35 | No.045 | 6.170 | NG |
| 35 | No.044 | 1.89 | NG | 26 | No.072 | 5.780 | NG |
| 36 | No.043 | 1.86 | NG | 12 | No.085 | 5.683 | NG |
| 55 | No.063 | 1.84 | NG | 33 | No.089 | 5.524 | NG |
| 52 | No.025 | 1.81 | NG | 28 | No.031 | 4.859 | NG |
| 47 | No.003 | 1.80 | NG | 25 | No.056 | 4.786 | NG |
| 8 | No.034 | 1.77 | NG | 10 | No.022 | 3.908 | NG |
| 54 | No.076 | 1.72 | NG | 19 | No.066 | 3.716 | NG |
| 12 | No.002 | 1.40 | NG | 27 | No.090 | 3.474 | NG |
| 18 | No.009 | 1.33 | OK | 8 | No.045 | 3.388 | NG |
| 20 | No.046 | 1.32 | OK | 21 | No.077 | 2.457 | NG |
| 48 | No.013 | 1.23 | OK | 16 | No.021 | 2.287 | NG |
| 26 | No.014 | 1.17 | OK | 5 | No.062 | 2.229 | NG |
| 31 | No.028 | 1.11 | OK | 11 | No.061 | 2.141 | NG |
| 50 | No.035 | 1.09 | OK | 7 | No.022 | 1.929 | NG |
| 21 | No.033 | 1.08 | OK | 6 | No.010 | 1.861 | NG |
| 19 | No.019 | 1.07 | OK | 15 | No.069 | 1.844 | NG |
| 34 | No.079 | 1.05 | OK | 9 | No.008 | 1.811 | NG |
| 32 | No.069 | 0.82 | OK | 23 | No.032 | 1.714 | NG |
| 2 | No.088 | 0.78 | OK | 3 | No.029 | 1.621 | NG |
| 27 | No.024 | 0.77 | OK | 20 | No.087 | 1.598 | NG |
| 22 | No.054 | 0.74 | OK | 14 | No.036 | 1.515 | NG |
| 42 | No.057 | 0.73 | OK | 17 | No.018 | 1.503 | NG |
| 49 | No.001 | 0.71 | OK | 30 | No.038 | 1.391 | NG |
| 13 | No.004 | 0.67 | OK | 1 | No.053 | 1.158 | OK |
| 6 | No.055 | 0.61 | OK | 18 | No.026 | 0.994 | OK |
| 28 | No.078 | 0.60 | OK | 31 | No.041 | 0.855 | OK |
| 4 | No.047 | 0.58 | OK | 4 | No.030 | 0.848 | OK |
| 7 | No.037 | 0.47 | OK | 24 | No.075 | 0.761 | OK |
| 15 | No.020 | 0.46 | OK | 2 | No.035 | 0.404 | OK |
| 14 | No.058 | 0.43 | OK | | | | |
| 11 | No.091 | 0.42 | OK | | | | |
| 39 | No.048 | 0.39 | OK | | | | |
| 9 | No.052 | 0.38 | OK | | | | |
| 5 | No.074 | 0.37 | OK | | | | |
| 29 | No.086 | 0.37 | OK | | | | |
| 23 | No.006 | 0.36 | OK | | | | |
| 10 | No.059 | 0.36 | OK | | | | |
| 33 | No.071 | 0.35 | OK | | | | |
| 40 | No.046 | 0.35 | OK | | | | |
| 38 | No.050 | 0.34 | OK | | | | |
| 24 | No.011 | 0.33 | OK | | | | |
| 1 | No.064 | 0.33 | OK | | | | |
| 45 | No.057 | 0.33 | OK | | | | |
| 37 | No.016 | 0.33 | OK | | | | |
| 17 | No.092 | 0.30 | OK | | | | |
| 41 | No.015 | 0.30 | OK | | | | |

F I G. 11

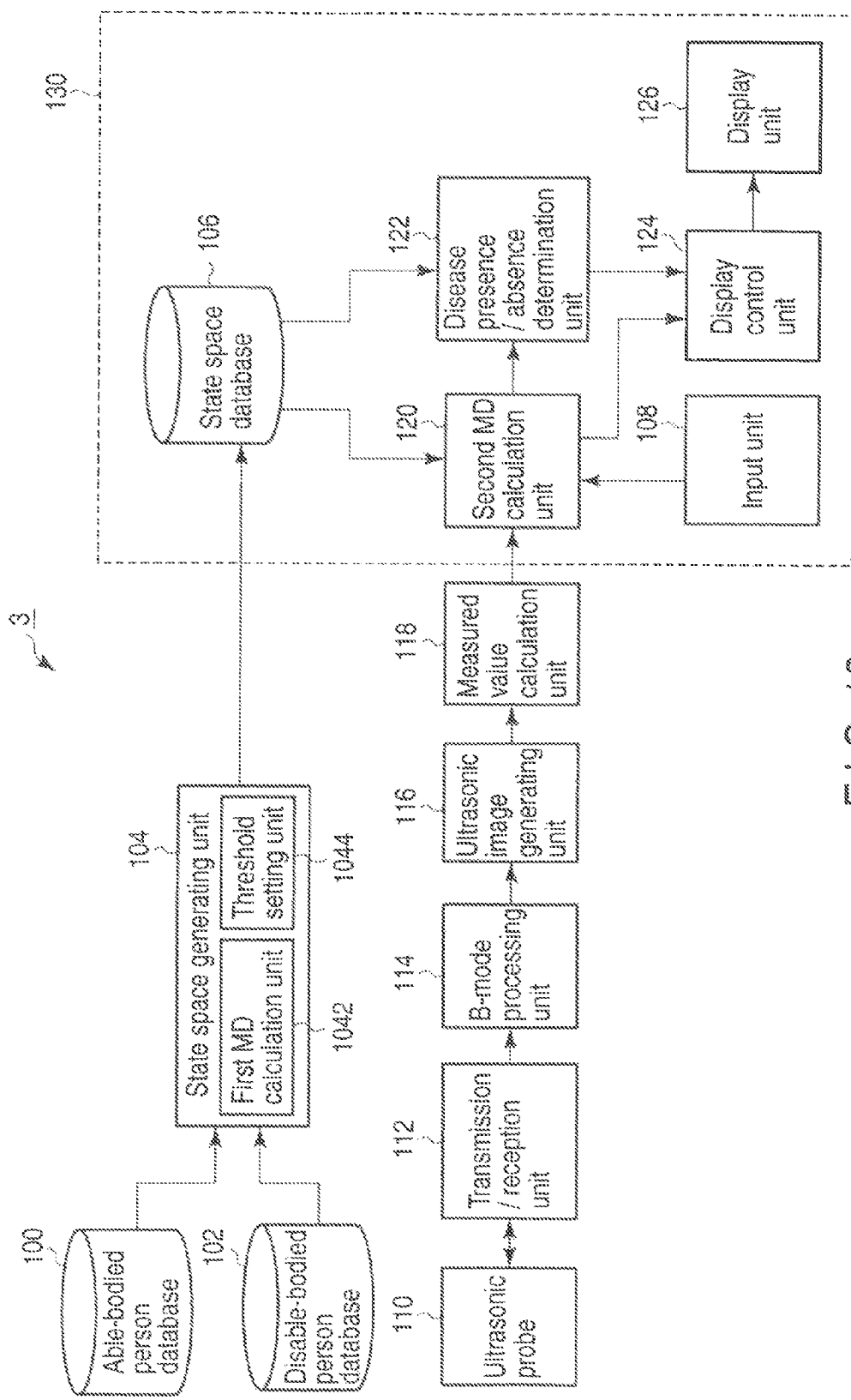
F I G. 12

ULTRASONIC DIAGNOSIS APPARATUS, AUTOMATIC SUPPORT APPARATUS, AND AUTOMATIC SUPPORT METHOD

CROSS-REFERENCE TO RELATED APPLICATIONS

This application is based upon and claims the benefit of priority form Japanese Patent Application No. 2009-152336, filed Jun. 26, 2009; the entire contents of which are incorporated herein by reference.

FIELD

Embodiments described herein relate generally to an ultrasonic diagnosis apparatus, automatic support apparatus, and automatic support method which are provided for ultrasonic diagnosis.

BACKGROUND

In medical examination for a circulatory organ or abdominal region, a doctor makes subjective diagnosis while referring to an electrocardiographic complex, ultrasonic images, and the like. For this reason, the doctor sometimes overlooks abnormality. If a doctor cannot discriminate abnormality with an electrocardiographic complex or ultrasonic image, redundant diagnosis is sometimes performed by using another diagnosis modality. This may lead to a deterioration in diagnosis efficiency.

BRIEF DESCRIPTION OF THE DRAWINGS

FIG. 1 is a block diagram showing the arrangement of an ultrasonic diagnosis apparatus according to the first embodiment;

FIG. 2 is a flowchart showing a typical procedure for the processing of automatically determining the presence/absence of a cardiac disease in a patient, which is implemented by the ultrasonic diagnosis apparatus in FIG. 1;

FIG. 5 is a view showing a concrete procedure from measured value calculation processing to Mahalanobis distance calculation processing by the ultrasonic diagnosis apparatus in FIG. 1;

FIG. 7 is a block diagram showing the arrangement of an ultrasonic diagnosis apparatus according to the second embodiment;

FIG. 10 is a view showing a list of measured values and diagnosis values of liver measurement items associated with a concrete example of the second embodiment;

FIG. 11 is a view showing a list of Mahalanobis distances and OK/NG judgments associated with able-bodied persons and disable-bodied persons in the concrete example in FIG. 10;

FIG. 12 is a block diagram showing the arrangement of an ultrasonic diagnosis apparatus according to the third embodiment;

DETAILED DESCRIPTION

Figure 3:
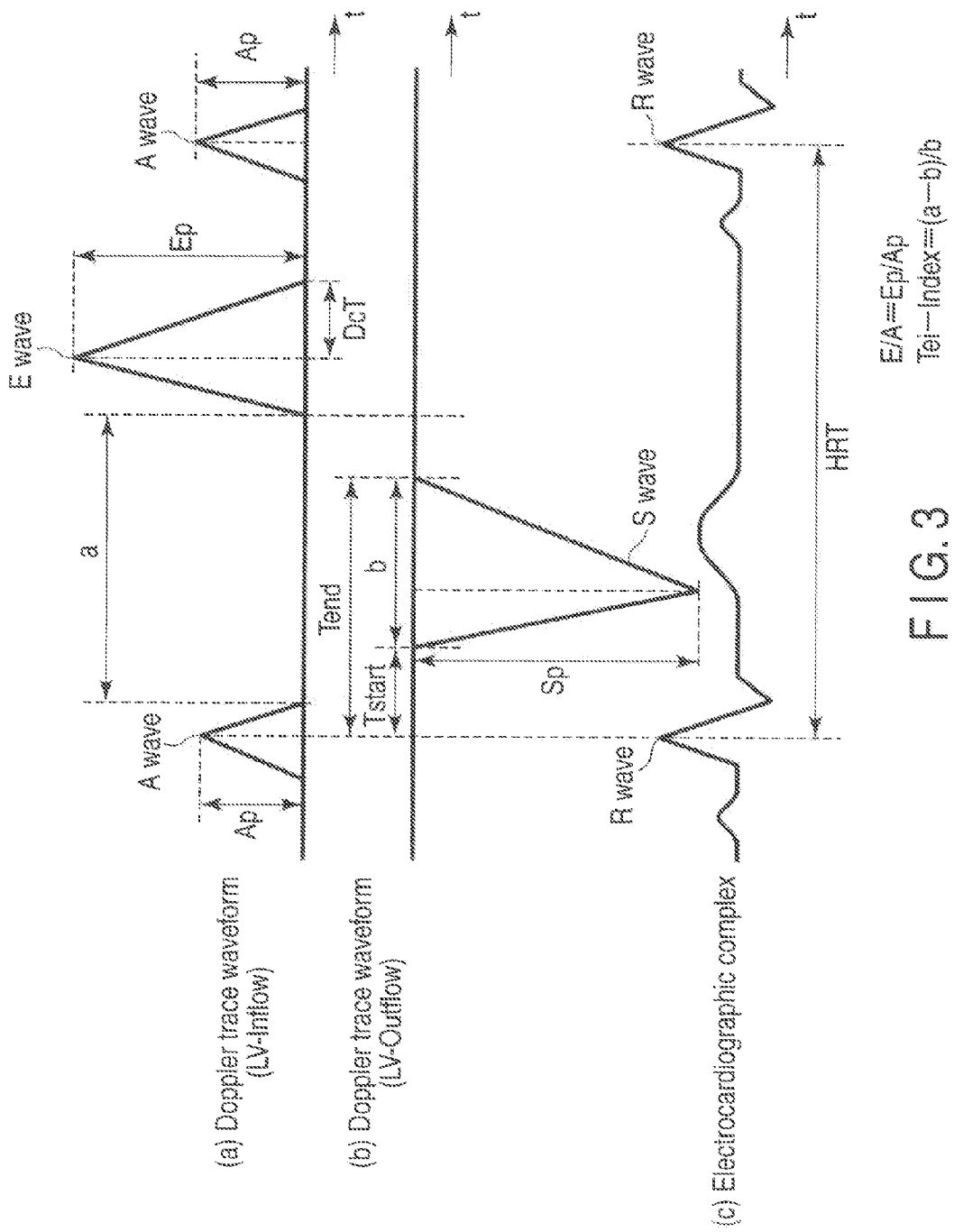
FIG. 3 is a chart for explaining measurement items associated with the LV-Inflow and LV-Outflow calculated by a measured value calculation unit in FIG. 1 and an electrocardiographic complex.

In general, according to one embodiment, an ultrasonic diagnosis apparatus according to an embodiment includes a storage unit, a ultrasonic probe, a transmission/reception unit, a measured value calculation unit, a distance calculation unit, and a determination unit. The storage unit stores data of a state space based on a first measured value of a measurement item associated with an able-bodied person. The transmission/reception unit transmits ultrasonic waves to a subject via an ultrasonic probe, receives ultrasonic waves reflected by the subject, and generates reception signals corresponding to the received ultrasonic waves. The measured value calculation unit calculates a second measured value of the measurement item associated with the subject based on the reception signals. The distance calculation unit calculates a Mahalanobis distance of the subject based on the state space and the second measured value. The determination unit compares the Mahalanobis distance with a threshold to determine whether the subject has the disease evaluated by the measurement item.

An ultrasonic diagnosis apparatus, automatic support apparatus, and automatic support method according to this embodiment will be described below with reference to the views of the accompanying drawing.

First Embodiment

The ultrasonic diagnosis apparatus, automatic support apparatus, and automatic support method according to the first embodiment aim at automatically determining by applying an MT (Mahalanobis Taguchi) system to blood flow information whether a subject (patient) has a cardiac disease. Note that the MT system may use any one of the following methods: the MT (Mahalanobis Taguchi) method, T (Taguchi) method, MTA (Mahalanobis Taguchi Ajoint) method, and TS (Taguchi Schmitt) method.

FIG. 1 is a block diagram showing the arrangement of an ultrasonic diagnosis apparatus 1 according to the first embodiment. As shown in FIG. 1, the ultrasonic diagnosis apparatus 1 includes an able-bodied person database 10, a disable-bodied person database 12, a state space generating unit 14, a measured value distribution model generating unit 16, and a state space database 18 which are used for offline analysis.

The able-bodied person database 10 stores measured values of cardiac measurement items associated with able-bodied persons. The cardiac measurement items are measurement items for the evaluation of a cardiac function. The measured values of the cardiac measurement items are calculated by, for example, automatic Doppler measurement based on a Doppler signal. This apparatus uses, for example, a measurement item associated with LV-Outflow (Left Ventricular Outflow) and a measurement item associated with LV-Inflow (Left Ventricular Inflow) as Doppler measurement items. The apparatus uses, as measurement items associated with LV-Outflow, for example, Sp (Systolic Point) which is the maximal value of an S wave (left ventricular ejection wave), VTI (Velocity Time Integral), Tstart which is the start time, Tend which is the end time, and the like. In addition, the measurement items associated with LV-Inflow include, for example, Ep which is the maximal value of an E wave (early diastolic flow wave), Ap which is the maximal value (atrial contraction flow), E/A which is the ratio between Ep and Ap, DcT (Deceleration Time) which is an falling interval of an E wave, and Tei-index. The Doppler measurement items may include measurement items based on differential/integral analysis on an LV-Outflow Doppler trace waveform and differential/integral analysis on an LV-Inflow Doppler trace waveform. The measurement items associated with differential/integral analysis include measurement items such as moving average, differential characteristic, integral characteristic, and time difference. The able-bodied person database 10 stores electrocardiographic complex data associated with able-bodied persons. The electrocardiograph supplies this electrocardiographic complex data. The able-bodied person database 10 may store the measured values of the cardiac measurement items based on electrocardiographic complexes. A method of calculating these measured values will be described later. Note that an able-bodied person is a person who, a doctor has determined, "has no cardiac disease" at the time of the acquisition of measured values. That is, each able-bodied person belongs to a space (unit space) which is homogeneous for purpose. Note that cardiac diseases include, for example, hypercardia, heart infarction, mitral regurgitation, aortic regurgitation, septal defect, and tachycardia-bradycardia syndrome. However, the types of cardiac diseases need not be limited to them. The first embodiment can also be applied to cardiac diseases other than the above diseases.

Like the able-bodied person database 10, the disable-bodied person database 12 stores measured values of cardiac measurement items associated with disable-bodied persons. A disable-bodied person is a person who, a doctor has determined, "has a cardiac disease" at the time of the acquisition of measured values. That is, a disable-bodied person does not belong to a unit space. The disable-bodied person database 12 also stores the measured value data associated with disable-bodied persons in correspondence with the types of cardiac diseases.

The state space generating unit 14 generates a multivariate state space based on measured values stored in the able-bodied person database 10. More specifically, the state space generating unit 14 includes a first MD calculation unit 142 and a threshold setting unit 144.

The first MD calculation unit 142 calculates the Mahalanobis distances (MDs) of able-bodied persons based on measured values stored in the able-bodied person database 10.

Mahalanobis distances are calculated by the following procedure. Assume that there are m able-bodied persons and n cardiac measurement items. First of all, the first MD calculation unit 142 calculates an average value Aj and standard deviation σj of measured value vectors vj=(v1$j$, v2$j$, ..., vmj) regarding measurement items j (1≤j≤n). The first MD calculation unit 142 then normalizes each measured value vector vj based on the calculated average value Aj and variance σj, and calculates a normalized measured value vector rj=(r1$j$, r2$j$, ..., rmj). The first MD calculation unit 142 calculates the average values Aj, standard deviations σj, and measured value vectors rj regarding all (n) measurement items. That is, the first MD calculation unit 142 calculates average vectors A=(A1, A2, ..., An), standard deviation vectors σ=(σ1, σ2, ..., σn), and m×n measured values rij (1≤i≤m, 1≤j≤n). The first MD calculation unit 142 calculates an n×n correlation matrix R and its inverse matrix $R^{-1}$ based on m×n measured values rij (1≤i≤m, 1≤j≤n). The first MD calculation unit 142 calculates Mahalanobis distances $yi^2=(1/n) \cdot rj \cdot R^{-1} \cdot rj^T$ regarding able-bodied persons i (1≤i≤m) based on the inverse matrix $R^{-1}$, the respective measured value vectors rj, and transposed vectors $rj^T$ of the respective measured values rj. The state space database 18 stores the data of these coefficient series (average values A, standard deviations σ, and inverse matrices $R^{-1}$) for the calculation of Mahalanobis distances and of the Mahalanobis distances $yi^2$ of the respective able-bodied persons.

The first MD calculation unit 142 also calculates, as in the case with the disable-bodied persons, the Mahalanobis distances of the disable-bodied persons based on the average value vectors A, variance vectors σ, and inverse matrices $R^{-1}$ calculated based on the measured values of the able-bodied persons.

The threshold setting unit 144 sets a threshold to the Mahalanobis distance located at the boundary between the Mahalanobis distances of the able-bodied persons and the Mahalanobis distances of the disable-bodied persons. More specifically, the threshold setting unit 144 generates the histogram of the Mahalanobis distances of the able-bodied persons and the Mahalanobis distances of the disable-bodied persons. The threshold setting unit 144 specifies the Mahalanobis distance located at the boundary between the Mahalanobis distances of the able-bodied persons and the Mahalanobis distances of the disable-bodied persons on the histogram, and sets a threshold to the specified Mahalanobis distance. Note that the user may set a threshold via an input unit (not shown).

The state space is the inverse matrices $R^{-1}$ regarding the able-bodied persons, with consideration given to the above threshold. In other words, the state space can be said to be defined by a set of the Mahalanobis distances of the able-bodied persons and the Mahalanobis distances of the disable-bodied persons. The state space functions as a scale used for measuring the degree of health of the cardiac function. More specifically, it is possible to generate state space data respectively for LV-Outflow and LV-Inflow or generate the data of one state space for them. Note that it is possible to generate a state space based on the measured values of measurement items based on a Doppler signal and the measured values of measurement items based on an electrocardiographic complex.

The measured value distribution model generating unit 16 generates a measured value distribution model for each cardiac disease by performing trend analysis on measured values associated with disable-bodied persons. The measured value distribution model indicates a typical measured value distribution unique to each disease over measurement items. Note that the measured value distribution model generating unit 16 uses, as the trend analysis, trend analysis on factors by the Taguchi method, the degree of contribution based on multivariate analysis, and the like.

The state space database 18 stores the state space data generated based on the measured values of able-bodied persons. In other words, the state space database 18 stores the average data, standard deviation data, inverse matrix data of a correlation matrix, Mahalanobis distance data, and threshold data which are calculated by the state space generating unit 14. The state space database 18 stores the measured value distribution model data generated by the measured value distribution model generating unit 16 for each disease type.

As shown in FIG. 1, the ultrasonic diagnosis apparatus 1 includes an electrocardiograph 20, an ultrasonic probe 22, a transmission/reception unit 24, a Doppler processing unit 26, a measured value calculation unit 28, a second Mahalanobis distance calculation unit 30, a disease presence/absence determination unit 32, a disease type discrimination unit 34, a display control unit 36, and a display unit 38 which are used for online analysis.

The electrocardiograph 20 generates the electrocardiographic complex data of a patient to be diagnosed. The electrocardiograph 20 supplies the generated electrocardiographic complex data to the measured value calculation unit 28 (to be described later).

The ultrasonic probe 22 transmits and receives ultrasonic waves. More specifically, the ultrasonic probe 22 includes piezoelectric transducers arranged one-dimensionally or two-dimensionally. A piezoelectric transducer is electroacoustic conversion element which converts an electrical pulse into an ultrasonic pulse (transmission ultrasonic wave) at the time of transmission, and converts a reflected ultrasonic wave (reception ultrasonic wave) into an electrical signal (reception signal) at the time of reception. The ultrasonic probe 22 is connected to the transmission/reception unit 24 through a cable.

The transmission/reception unit 24 repeatedly scans a patient with ultrasonic waves via the ultrasonic probe 22. In other words, the transmission/reception unit 24 transmits ultrasonic waves to the patient via the ultrasonic probe 22, receives the ultrasonic waves reflected by the patient, and generates a reception signal corresponding to the received ultrasonic waves.

For ultrasonic transmission, the transmission/reception unit 24 includes a rate pulse generator, transmission delay circuit, and pulser. The rate pulse generator generates rate pulses for determining the repetition period of transmission ultrasonic waves, and supplies the generated rate pulses to the transmission delay circuit. The transmission delay circuit includes independent delay circuits equal in number (N channels) to the piezoelectric transducers. The transmission delay circuit gives rate pulses delay times for converging transmission ultrasonic waves to a predetermined depth so as to obtain a narrow beam width in transmission and delay times for radiating transmission ultrasonic waves in a predetermined direction. The pulser includes independent driving circuits for the N channels. The pulser generates driving pulses for driving the piezoelectric transducers based on rate pulses.

For ultrasonic reception, the transmission/reception unit 24 includes a preamplifier, A/D converter, reception delay circuit, and adder. The preamplifier amplifies reception signals corresponding to the N channels from the piezoelectric transducers. The A/D converter converts the amplified reception signals corresponding to the N channels into digital signals. The reception delay circuit gives the reception signals corresponding to the N channels convergence delay times for converging reflected ultrasonic waves from a predetermined depth and deflection delay times for setting reception directivity relative to a predetermined direction. The adder performs phased addition of reception signals from the reception delay circuit (adds the reception signals obtained from a predetermined direction upon phasing them).

The Doppler processing unit 26 generates a Doppler signal (IQ signal) by performing quadrature detection of a reception signal from the transmission/reception unit 24. As is well known, a Doppler signal is constituted by a real component (I component) and an imaginary component (Q component).

The measured value calculation unit 28 calculates measured values associate with Doppler measurement items based on Doppler signals from the Doppler processing unit 26. These Doppler measurement items are the same as those used for the generation of the state space.

The second MD calculation unit 30 calculates the Mahalanobis distance of a patient in the state space stored in the state space database 18. That is, the second MD calculation unit 30 calculates a Mahalanobis distance based on the plurality of measured values of the plurality of measurement items calculated by the measured value calculation unit 28 and the state space. More specifically, the second MD calculation unit 30 normalizes measured values vp ($=v1p, v2p, \ldots, vnp$) associated with a patient based on the average value vector A and standard deviation $\sigma$ described above, and calculates normalized measured values rp=($r1p, r2p, \ldots, rnp$). The second MD calculation unit 30 calculates Mahalanobis distance $yp^2 = (1/n) \cdot rp \cdot R^{-1} \cdot rp^T$ associated with the patient based on the measured values rp and the inverse matrix $R^{-1}$.

The disease presence/absence determination unit 32 compares the Mahalanobis distance $yp^2$ of the patient with a threshold T to determine whether the patient has a cardiac disease. More specifically, if Mahalanobis distance $yp^2$<threshold T, the disease presence/absence determination unit 32 determines that the patient has no cardiac disease. If $yp^2$>T, the disease presence/absence determination unit 32 determines that the patient has a cardiac disease.

The disease type discrimination unit 34 discriminates the type of cardiac disease which the patient has with a high probability by performing trend analysis on measured values associated with the patient. More specifically, the disease type discrimination unit 34 calculates the similarity between the distribution of measured values associated with the patient and the measured value distribution model for each type of cardiac disease stored in the state space database 18. The disease type discrimination unit 34 then determines a cardiac disease corresponding to the measured value distribution model exhibiting the maximum similarity as the cardiac disease which the patient has with a high probability.

The display control unit 36 displays the Mahalanobis distance of the patient and the determination result indicating the presence/absence of a cardiac disease on the display unit 38. The display control unit 36 displays the trend analysis result obtained by the disease type discrimination unit 34 on the display unit 38.

The following is a description of the processing of automatically determining the presence/absence of a cardiac disease in a patient, which is implemented by the ultrasonic diagnosis apparatus 1. FIG. 2 is a flowchart showing a typical procedure for automatic determination processing. As shown in FIG. 2, first of all, the transmission/reception unit 24 repeatedly scans the heart of a patient in the Doppler mode via the ultrasonic probe 22 (step SA1). During scanning in the Doppler mode, the Doppler processing unit 26 generates a Doppler signal by performing Doppler processing for the reception signals acquired via the ultrasonic probe 22. In order to improve the accuracy of measured values, the Doppler processing unit 26 may remove clutter components caused by the respiratory or pulsatory movement of the heart and the like contained in the Doppler signal.

When a Doppler signal is generated, the measured value calculation unit 28 calculates the measured values of cardiac measurement items based on the Doppler signal (step SA2). The following is a description of a concrete example of measured value calculation processing by the measured value calculation unit 28.

For example, the measured value calculation unit 28 generates the Doppler trace waveform data associated with LV-Inflow based on a Doppler signal. The measured value calculation unit 28 then calculates measurement items associated with LV-Outflow from the Doppler trace waveform associated with LV-Inflow by using an automatic Doppler measurement technique. Likewise, the measured value calculation unit 28 calculates measurement items associated with LV-Outflow based on the Doppler signal. The measured value calculation unit 28 may also calculate the feature amount of an electrocardiographic complex by applying an existing processing technique to the electrocardiographic complex.

FIG. 3 is a chart for explaining measurement items associated with LV-Inflow, LV-Outflow, and electrocardiographic complex which are calculated by the measured value calculation unit 28. In FIG. 3, (a), (b), and (c) schematically show the Doppler trace waveform of LV-Inflow, the Doppler trace waveform of LV-Outflow, and an electrocardiographic complex, respectively.

As shown in (a) in FIG. 3, the measurement items associated with LV-Inflow include Ep, Ap, E/A, DcT, and Tei-index. Ep represents the maximum amplitude of an E wave, i.e., the maximum blood flow velocity. Ap represents the maximum amplitude of an A wave, i.e., the maximum blood flow velocity. Clinically, growing old tends to decrease Ep and increase Ap. E/A is calculated from Ep/Ap. DcT is a deceleration time interval of an E wave. Tei-index is defined by "Tei-index"= (a−b)/b. In this case, the parameter a is defined by the time interval from the end time of the A wave to the start time of the E wave. The parameter b is defined by the continuation time of an S wave. Tei-index is known as a comprehensive evaluation index for left ventricular systolic performance and left ventricular diastolic performance.

As shown in (b) in FIG. 3, the measurement items associated with LV-Outflow include Sp, VTI, Tstart, and Tend. Sp represents the maximum amplitude of an S wave, i.e., the maximum blood flow velocity. Tstart represents the time interval from the start time of an R wave of an electrocardiographic complex to the start time of an S wave. Tend represents the time interval from the start time of an R wave of the electrocardiographic complex to the end time of an S wave.

As shown in (c) in FIG. 3, the measurement items of an electrocardiographic complex include HRT. HRT is defined by the time interval between adjacent R waves.

An example of other measurement items will be described. The measured value calculation unit 28 generates Doppler spectrum data associated with LV-Inflow by performing FFT (Fast Fourier Transform) for a Doppler signal. The measured value calculation unit 28 then calculates the measured values of measurement items associated with LV-Inflow from the Doppler spectrum associated with LV-Inflow. Likewise, the measured value calculation unit 28 generates Doppler spectrum data associated with LV-Outflow from a Doppler signal, and calculates the measured values of measurement items associated with LV-Outflow from the generated Doppler spectrum.

Still another example of other measurement items will be described. The measured value calculation unit 28 may calculate waveform feature amounts of the Doppler trace waveform, e.g., the moving average, differential characteristic, integral characteristic, and time difference associated with LV-Inflow and LV-Outflow, by performing differential/integral analysis on the Doppler trace waveform associated with LV-Inflow and LV-Outflow. The calculated waveform feature amounts are used as the measured values of the Doppler measurement items.

Still another example of other measurement items will be described. The measured value calculation unit 28 calculates the average flow velocity value and variance of a blood flow based on a Doppler signal. The calculated average flow velocity value, variance, and the like are used as the measured values of the Doppler measurement items.

Note that it is not necessary to use all the cardiac measurement items described above for the automatic determination of a disease. It is possible to use, for example, cardiac measurement items, of the above cardiac measurement items, which are set by the user.

When the measured values of the cardiac measurement items are calculated in the above manner, the second MD calculation unit 30 calculates the Mahalanobis distance of the patient (step SA3). More specifically, the second MD calculation unit 30 calculates the Mahalanobis distance of the patient based on the measured values calculated in step SA2 and the state space associated with able-bodied persons. This state space associated with able-bodied persons is generated in advance by the state space generating unit 14 before Doppler-mode scanning on the patient.

When the Mahalanobis distance of the patient is calculated, the disease presence/absence determination unit 32 compares the Mahalanobis distance calculated in step SA3 with a preset threshold to determine whether the patient has a cardiac disease (step SA4). The threshold is generated in advance by the state space generating unit 14 before Doppler-mode scanning on the patient. If the Mahalanobis distance of the patient is larger than the threshold, the disease presence/absence determination unit 32 determines that the patient has a cardiac disease. If the Mahalanobis distance of the patient is smaller than the threshold, the disease presence/absence determination unit 32 determines that the patient has no cardiac disease.

When the disease presence/absence determination unit 32 determines the presence/absence of a cardiac disease, the display control unit 36 displays the determination result obtained in step SA4 on the display unit 38 (step SA5).

Figure 4:
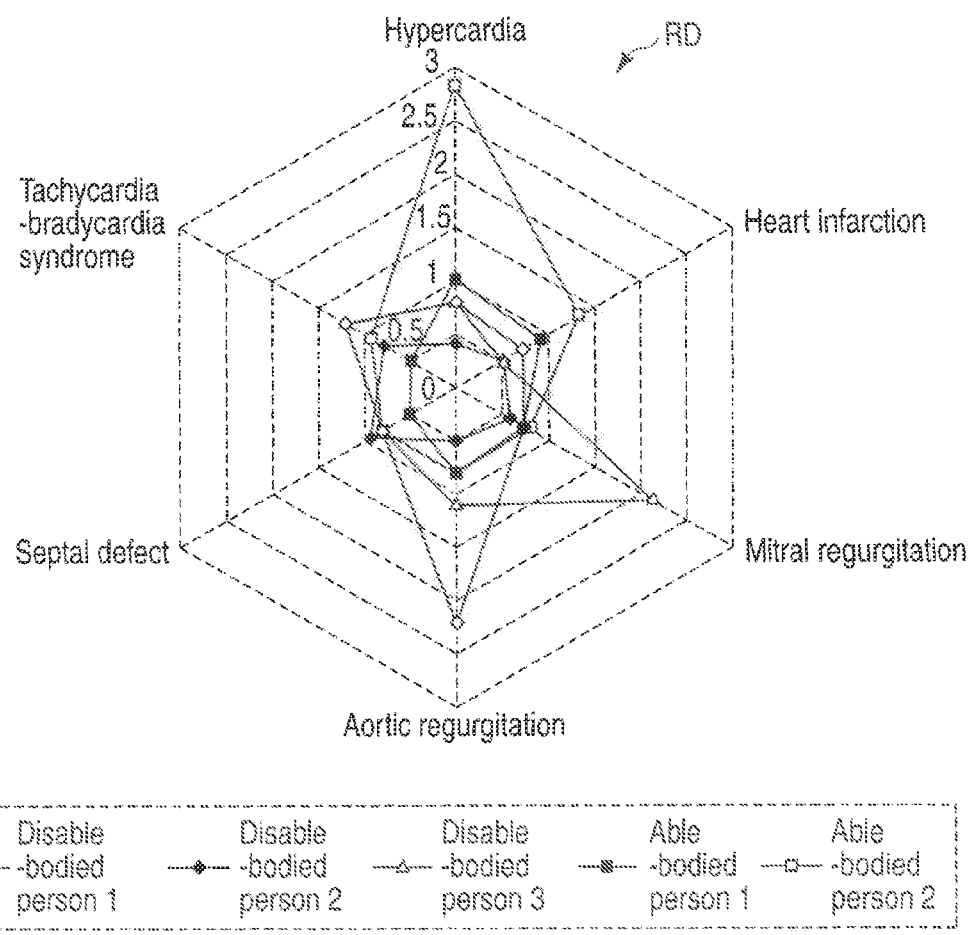
FIG. 4 is a view showing the radar chart displayed on a display unit by a display control unit in FIG. 1.

With the above operation, this apparatus terminates the processing of automatically determining the presence/absence of a cardiac disease in the patient. Note that the above automatic determination processing is merely an example, and the automatic determination processing according to the first embodiment is not limited to this. If, for example, the disease presence/absence determination unit 32 determines in step SA4 that the patient has a cardiac disease, the disease type discrimination unit 34 may discriminate the type of cardiac disease in the above manner. For example, the disease type discrimination unit 34 calculates the similarity between the distribution of the measured values calculated in step SA2 and the measured value distribution model for each cardiac disease type stored in the state space database 18. When this similarity is calculated, the display control unit 36 displays a radar chart RC like that shown in FIG. 4. The radar chart RC quantitatively indicates the risk of having each cardiac disease. The higher the similarity, the higher the risk.

A concrete example of automatic cardiac disease discrimination processing will be described below. FIG. 5 is a view showing a concrete procedure from measured value calculation processing to Mahalanobis distance calculation processing. As shown in FIG. 5, assume that this processing uses, for example, a Doppler trace waveform associated with LV-Inflow of able-bodied persons, a Doppler trace waveform associated with LV-Inflow of disable-bodied persons, a Doppler trace waveform associated with LV-Outflow of the able-bodied persons, and a Doppler trace waveform associated with LV-Outflow of the disable-bodied persons to calculate the Mahalanobis distance. The amplitude of a Doppler trace waveform may be normalized with the amplitude value at the start time being "0". Note that it is possible to use a Doppler trace waveform whose amplitude is not normalized. In addition, a portion exhibiting relatively small errors due to sampling may be used as a Doppler trace waveform.

The measured value calculation unit 28 calculates a waveform feature amount from a Doppler trace waveform associated with LV-Outflow based on the differential-integral method. The measured value calculation unit 28 calculates the measured values of measurement items associated with LV-Outflow from a Doppler trace waveform based on automatic Doppler measurement. For example, the measured value calculation unit 28 uses "HRT", "Sp", "VTI", "Tstart", "Tend", and the like as measurement items associated with LV-Outflow. The first MD calculation unit 142 and the second MD calculation unit 30 calculate Mahalanobis distances based on waveform feature amounts associated with LV-Outflow and the measured values of the measurement items. It was found as a result of simulation that "Sp", "VTI", and the leading edge of a waveform were effective.

Likewise, the measured value calculation unit 28 calculates waveform feature amounts from a Doppler trace waveform associated with LV-Inflow based on the differential-integral method. The measured value calculation unit 28 also calculates the measured values of the measurement items associated with LV-Inflow from the Doppler trace waveform based on automatic Doppler measurement. The measured value calculation unit 28 used, for example, "HRT", "Ep", "Ap", "E/A", "DcT", and "Tei-index" as measurement items associated with LV-Inflow. The first MD calculation unit 142 and the second MD calculation unit 30 calculate a Mahalanobis distance based on waveform feature amounts associated with LV-Outflow and the measured values of the measurement items. It was found as a result of simulation that "Ep", "Ap", and "Tei-index" were effective.

Figure 6:
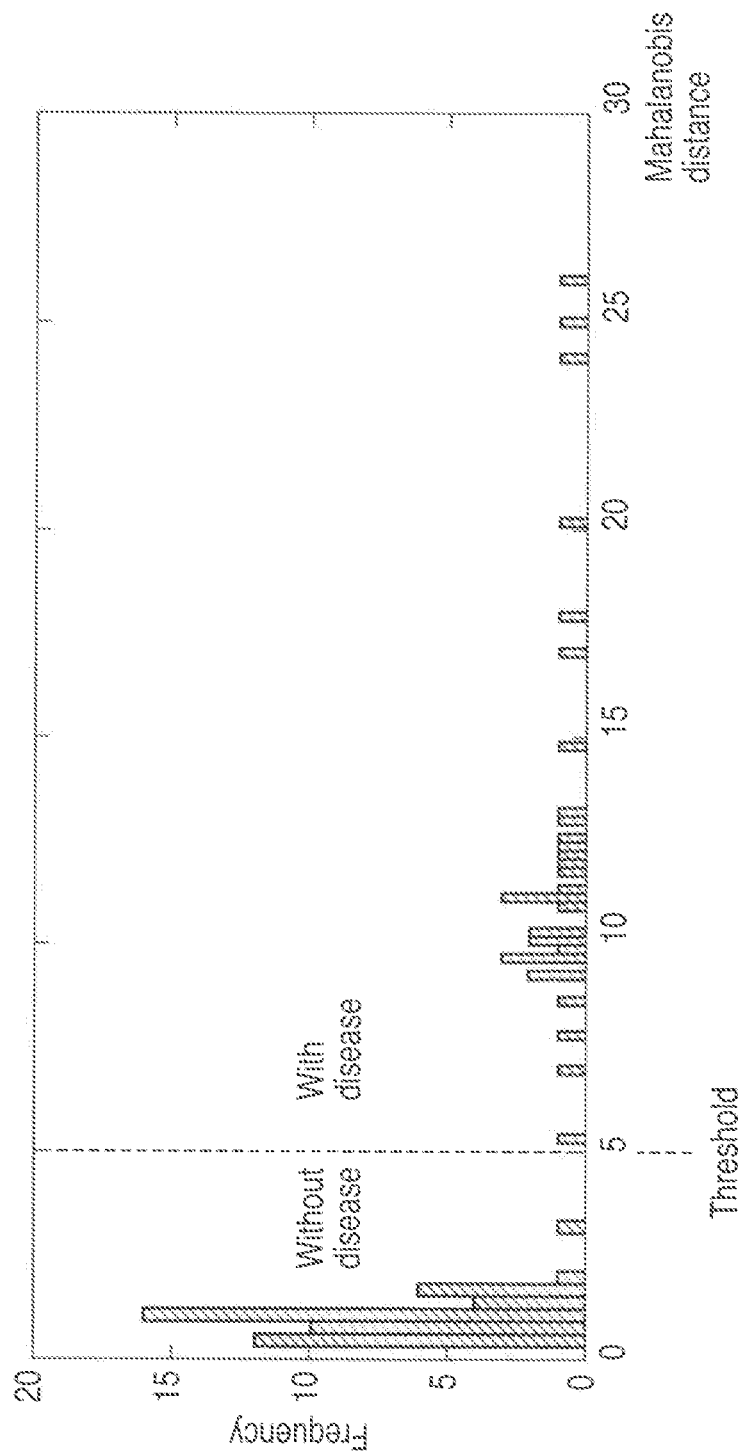
FIG. 6 is a graph showing a Mahalanobis distance histogram according to a concrete example of the first embodiment.

Note that the number of able-bodied persons as samples is 10, and the number of disable-bodied persons is 10. The number of able-bodied persons as samples associated with LV-Inflow corresponds to 47 heart beats, and the number of disable-bodied persons as samples associated with LV-Inflow corresponds to 33 heart beats. FIG. 6 is a graph showing the Mahalanobis distance histogram generated under this condition. As shown in FIG. 6, able-bodied persons and disable-bodied persons are separated at a Mahalanobis distance 4.6. That is, the able-bodied persons exhibit 4.6 or less, and the disable-bodied persons exhibit 4.6 or more. Therefore, the threshold for this state space was set to "4.6". The accuracy of diagnosis of the presence/absence of a disease using this state space was 100%.

In addition, the first embodiment used, for example, "Sp", "VTI", and "Tstart" as measurement items for the generation of a state space associated with LV-Outflow. Note that the number of able-bodied persons as samples associated with LV-Outflow corresponded to 58 heart beats, and the number of disable-bodied persons as samples corresponded to 31 heart beats. The threshold was set to "5". The accuracy of diagnosis of the presence/absence of a disease using this state space was 94.8%.

As described above, the ultrasonic diagnosis apparatus 1 according to the first embodiment generates in advance a multivariate state space in the MT system based on the measured values of measurement items for the evaluation of a cardiac function. At the time of diagnosis, the ultrasonic diagnosis apparatus 1 scans the heart of a patient to be diagnosed with ultrasonic waves and calculates the measured values of cardiac measurement items based on a Doppler signal. The ultrasonic diagnosis apparatus 1 then calculates the Mahalanobis distance of the patient in the state space generated in advance. The ultrasonic diagnosis apparatus 1 compares the Mahalanobis distance with the threshold to automatically determine whether the patient has a cardiac disease. It was found as a result of simulation that the accuracy of this determination performance was about 95%. The determination performance is the ability to correctly determine that a patient who is determined to "have a cardiac disease" "has a cardiac disease", and that a patient who is determined to "have no cardiac disease" "has no cardiac disease". Therefore, the ultrasonic diagnosis apparatus 1 can easily and quickly determine whether a patient has a cardiac disease, with an accuracy almost equal to that when a doctor subjectively makes determination as in conventional cases. The first embodiment can therefore provide the ultrasonic diagnosis apparatus 1 and the automatic support method which improve diagnosis efficiency.

Note that this embodiment need not implement the disease presence/absence determination function, the disease type discrimination function, and the like in the ultrasonic diagnosis apparatus 1. For example, as shown in FIG. 1, the embodiment may be an automatic support apparatus (CAD) 40 including the state space database 18, second MD calculation unit 30, disease presence/absence determination unit 32, disease type discrimination unit 34, display control unit 36, and display unit 38. The automatic support apparatus 40 is connected to the ultrasonic diagnosis apparatus including the ultrasonic probe 22, transmission/reception unit 24, Doppler processing unit 26, and measured value calculation unit 28 via a network or the like. The automatic support apparatus 40 receives the data of measured values associated with a patient from the measured value calculation unit 28, and stores the data in, for example, the internal memory of the second MD calculation unit 30. In response to a start request from the user, the automatic support apparatus 40 calculates the Mahalanobis distance of the patient based on the measured values and the state space, and automatically determines by using the calculated Mahalanobis distance whether the patient has a cardiac disease.

The ultrasonic diagnosis apparatus 1 generates a state space based on the measured values obtained from a Doppler signal and an electrocardiographic complex, determines the presence/absence of a cardiac disease, and discriminates the types of cardiac disease. However, the operations of the ultrasonic diagnosis apparatus 1 need not be limited to them. The ultrasonic diagnosis apparatus 1 may generate a state space, determine the presence/absence of a cardiac disease, and discriminate the type of cardiac disease, with consideration being also given to measured values from other modalities such as an X-ray computed tomography apparatus and a magnetic resonance imaging apparatus.

Second Embodiment

An ultrasonic diagnosis apparatus, automatic support apparatus, and automatic support method according to the second embodiment aim at automatically determining, by applying an MT system to tissue information associated with the liver, whether the patient has a liver disease.

FIG. 7 is a block diagram showing the arrangement of an ultrasonic diagnosis apparatus 2 according to the second embodiment. As shown in FIG. 7, the ultrasonic diagnosis apparatus 2 includes an able-bodied person database 50, a disable-bodied person database 52, a state space generating unit 54, a measured value distribution model generating unit 56, and a state space database 58 which are used for offline analysis.

The able-bodied person database 50 stores measured values of liver measurement items associated with able-bodied persons. The liver measurement items are measurement items for the evaluation of a liver function. For example, the liver measurement items include the image feature amount of a local region in a liver region included in an ultrasonic image. The liver measurement items also include measurement items for liver function examination by an automatic analyzer. That is, the able-bodied person database 50 may store measured values of liver function examination items. For example, ALP and GLP are used as liver function examination items. Note that an able-bodied person is a person determined by a doctor to "have no liver disease" at the time of the acquisition of measured values. That is, each able-bodied person belongs to a unit space. The types of liver diseases include, for example, hepatocirrhosis, hepatic cancer, and fatty liver. However, the types of liver diseases need not be limited to them. The second embodiment can be applied to liver diseases other than those described above.

Like the able-bodied person database 50, the disable-bodied person database 52 stores measured values of liver measurement items associated with disable-bodied persons. A disable-bodied person is a person determined by a doctor to "have a liver disease" at the time of the acquisition of measured values. That is, each disable-bodied person does not belong to a unit space. The disable-bodied person database 52 also stores the measured value data associated with disable-bodied persons in correspondence with the types of diseases.

The state space generating unit 54 generates a multivariate state space based on measured values of liver measurement items stored in the able-bodied person database 50. More specifically, the state space generating unit 54 includes a first MD calculation unit 542 and a threshold setting unit 544. The first MD calculation unit 542 calculates an inverse matrix $R^{-1}$ based on measured values of liver measurement items associated with able-bodied persons in accordance with a procedure similar to that in the first embodiment. The first MD calculation unit 542 then calculates the Mahalanobis distances of the respective able-bodied persons based on measured values of liver measurement items. The first MD calculation unit 542 calculates the Mahalanobis distances of the respective disable-bodied persons based on measured values of liver measurement items stored in the disable-bodied person database 52. The threshold setting unit 544 sets a threshold to the Mahalanobis distance located at the boundary between the Mahalanobis distances of the able-bodied persons and the Mahalanobis distances of the disable-bodied persons.

The measured value distribution model generating unit 56 generates a measured value distribution model for each liver disease by performing trend analysis on measured values associated with disable-bodied persons.

The state space database 58 stores the state space data generated based on the measured values associated with the able-bodied persons. The state space database 58 stores the measured value distribution model data for each liver disease type generated by the measured value distribution model generating unit 56.

As shown in FIG. 7, the ultrasonic diagnosis apparatus 2 includes an input unit 60, an ultrasonic probe 62, a transmission/reception unit 64, a B-mode processing unit 66, an ultrasonic image generating unit 68, a measured value calculation unit 70, a second MD calculation unit 72, a disease presence/absence determination unit 74, a disease type discrimination unit 76, a display control unit 78, and a display unit 80 which are used for online analysis.

The input unit 60 receives the measured value data of the liver measurement items associated with the patient which are measured by the automatic analyzer. The liver measurement items measured by this automatic analyzer include ALP and GLP described above. The input unit 60 supplies the input measured value data to the second MD calculation unit 72 (to be described later).

The transmission/reception unit 64 scans a scanning region including the liver of the patient with ultrasonic waves via the ultrasonic probe 62.

The B-mode processing unit 66 performs B-mode processing for a reception signal from the transmission/reception unit 64, and generates a B-mode signal whose signal strength is expressed by a luminance level. More specifically, the B-mode processing unit 66 performs envelope detection and logarithmic transformation for a reception signal. The generated B-mode signal is supplied to the ultrasonic image generating unit 68.

The ultrasonic image generating unit 68 generates the data of an ultrasonic image of the liver of the patient based on the B-mode signal from the B-mode processing unit 66. The generated ultrasonic image is included in the liver region. The generated ultrasonic image data is supplied to the measured value calculation unit 70.

The measured value calculation unit 70 calculates measured values of liver measurement items associated with the patient based on the liver region of the ultrasonic image from the ultrasonic image generating unit 68.

The second MD calculation unit 72 calculates the Mahalanobis distance of the patient in the state space stored in the state space database 58. In this case, the second MD calculation unit 72 may calculate a Mahalanobis distance in consideration of measured values from the automatic analyzer which are input from the input unit 60.

The disease presence/absence determination unit 74 compares the Mahalanobis distance of the patient with the threshold set by the threshold setting unit 544 to determine whether the patient has a liver disease.

The disease type discrimination unit 76 discriminates the type of liver disease which the patient has with a high probability by performing trend analysis on measured values associated with the patient. More specifically, the disease type discrimination unit 76 calculates the similarity between the distribution of the plurality of measured values associated with the patient and the measured value distribution model for each type of liver disease stored in the state space database. The disease type discrimination unit 76 then determines a liver disease corresponding to the measured value distribution model exhibiting the maximum similarity as the liver disease which the patient has with a high probability.

The display control unit 78 displays the Mahalanobis distance of the patient and the determination result indicating the presence/absence of a liver disease on the display unit 80. If the disease presence/absence determination unit 74 determines that the patient has a liver disease, the display control unit 78 displays the trend analysis result obtained by the disease type discrimination unit 76 on the display unit 80.

Figure 8:
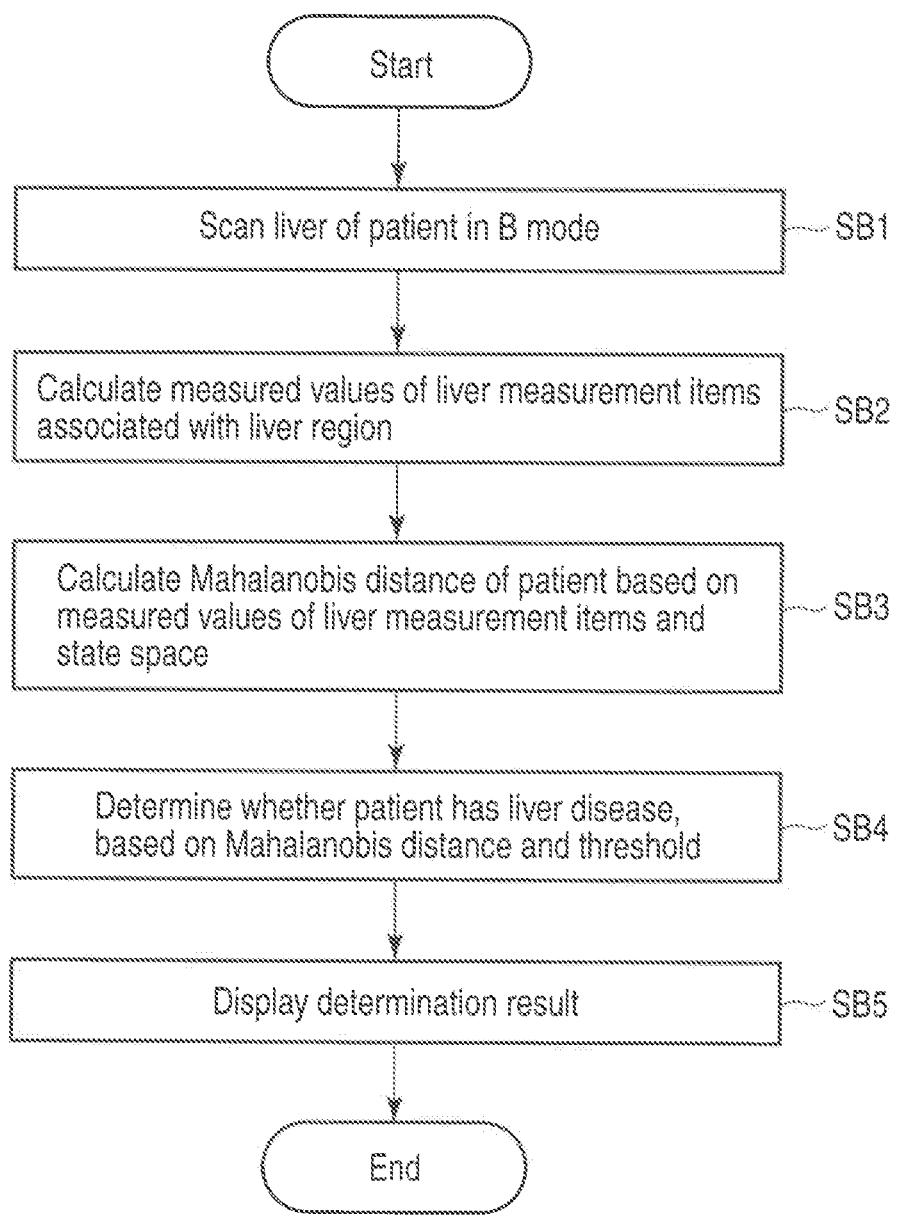
FIG. 8 is a flowchart showing a typical procedure for the processing of automatically determining the presence/absence of a liver disease in a patient, which is implemented by the ultrasonic diagnosis apparatus in FIG. 7.

The following is a description of the processing of automatically determining the presence/absence of a liver disease in a patient, which is implemented by the ultrasonic diagnosis apparatus 2. FIG. 8 is a flowchart showing a typical procedure for the processing of automatically determining the presence/absence of a liver disease in a patient. As shown in FIG. 8, first of all, the transmission/reception unit 64 repeatedly scans the liver of the patient in the B mode via the ultrasonic probe 62 (step SB1). During B-mode scanning, the B-mode processing unit 66 generates a B-mode signal by performing B-mode processing for the reception signals acquired via the ultrasonic probe 62. The ultrasonic image generating unit 68 generates the data of an ultrasonic image of the liver of the patient based on the generated B-mode signal.

When the ultrasonic image is generated, the measured value calculation unit 70 calculates the measured values of liver measurement items based on the ultrasonic image (step SB2). A concrete example of the processing of calculating the measured values of liver measurement items by the measured value calculation unit 70 will be described below.

Figure 9:
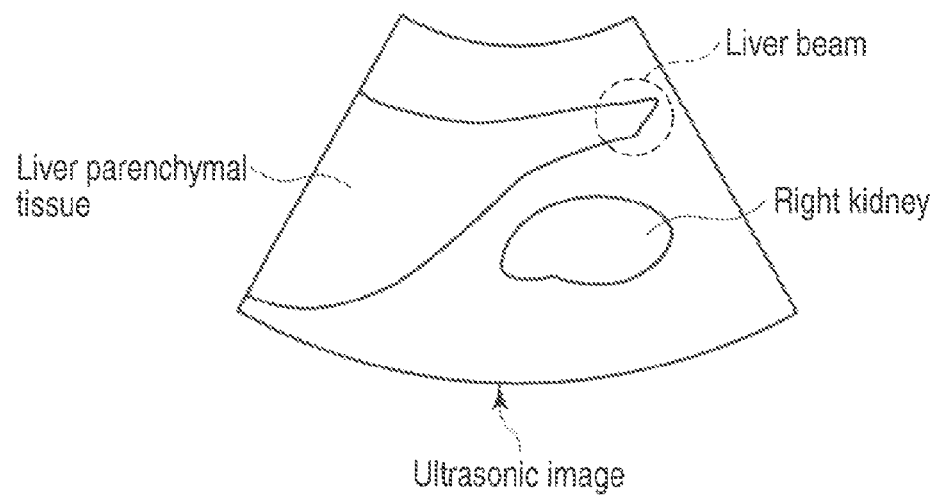
FIG. 9 is a view for explaining liver measurement items calculated by a measured value calculation unit in FIG. 7.

FIG. 9 is a view for explaining liver measurement items. FIG. 9 shows an ultrasonic image including the liver region and right kidney region of a patient. As shown in FIG. 9, the liver region has a distal end (edge) portion called a liver beam. It is known that this liver beam becomes thick along with a progress of disease like hepatitis→hepatocirrhosis→hepatic cancer. The liver is mostly formed from the liver parenchymal tissue. It is known that this liver parenchymal tissue becomes rough, i.e., fibrous, along with a progress of disease like hepatitis→hepatocirrhosis→hepatic cancer. It is also known that the surface of the liver becomes rough to exhibit a rough surface along with a progress of disease like hepatitis→hepatocirrhosis→hepatic cancer. In this manner, along with the progress of a liver disease, the liver surface exhibits a larger change in shape or the liver parenchyma becomes more fibrous. Therefore, as liver measurement items, various image feature amounts associated with a liver region are used. In addition, the kidneys are located near the liver. For this reason, as liver measurement items, liver measurement items such as a liver-kidney contrast is used. A liver-kidney contrast is defined by the ratio between the echo strength of the liver and the echo strength of the renal cortex. If the echo strength of the liver is higher than that of the renal cortex, the suspicion of fatty liver is high.

More specifically, for example, as liver measurement items, the following image feature amounts are used: the shape of a liver region, granularity using a correlation function, contrast, and luminance value continuity. The local regions of the liver region include the peripheral portion, parenchymal portion, distal end (edge) portion, and surface portion of the liver region. It is possible to give consideration to a kidney region located near the liver region as an image feature amount. It is also possible to use the subcutaneous fat thickness of an abdominal region or the like as a liver measurement item. Furthermore, it is possible to use the above liver-kidney contrast as a liver measurement item.

When measured values are calculated in the above manner, the second MD calculation unit 72 calculates the Mahalanobis distance of the patient (step SB3). More specifically, the second MD calculation unit 72 calculates the Mahalanobis distance of the patient based on the measured values calculated in step SB2 and the state space associated with able-bodied persons. Note that it is possible to use the measured values of liver function examination items such as ALP and GLP for the calculation of the Mahalanobis distance. The state space associated with the able-bodied persons is generated in advance by the state space generating unit 54 before B-mode scanning on the patient.

When the Mahalanobis distance of the patient is calculated, the disease presence/absence determination unit 74 compares the Mahalanobis distance calculated in step SB3 with a preset threshold to determine whether the patient has a liver disease (step SB4). The threshold is generated in advance by the state space generating unit 54 before B-mode scanning on the patient. If the Mahalanobis distance of the patient is larger than the threshold, the disease presence/absence determination unit 74 determines that the patient has a liver disease. If the Mahalanobis distance is smaller than the threshold, the disease presence/absence determination unit 74 determines that the patient has no liver disease.

When the disease presence/absence determination unit 74 determines the presence/absence of a liver disease, the display control unit 78 displays the determination result obtained in step SB4 on the display unit 80 (step SB5).

With the above operation, this apparatus terminates the processing of automatically determining the presence/absence of a liver disease in a patient.

A concrete example of automatic liver disease discrimination processing will be described below. FIG. 10 is a view showing a list of the measured values of liver measurement items and diagnosis values. As shown in FIG. 10, this apparatus used "edge", "surface", "parenchymal", "splenomegaly", "deformity", and "subcutaneous fat [mm]" as liver measurement items. US scores of three levels are used for "edge", "surface", "parenchymal", "splenomegaly", and "deformity". A diagnosis value quantitatively represents the hardness of the liver. More specifically, a diagnosis value corresponds to the propagation velocity of an elastic wave in the liver which is measured by using an ultrasonic wave. This diagnosis value is not used as a liver measurement item. The diagnosis value is used to evaluate the coincidence between the diagnosis result (indicating the presence/absence of a disease) according to this embodiment and the diagnosis result obtained by another diagnosis modality and to compare the diagnosis performance of this embodiment with that of another diagnosis modality.

FIG. 11 is a view showing a list of Mahalanobis distances of able-bodied persons and disable-bodied persons and OK/NG judgments. The Mahalanobis distances were calculated by using the measured values of the six items in FIG. 10. "OK" of the OK/NG judgments indicates that the diagnosis value is smaller than a threshold. "NG" of the OK/NG judgments indicates that the diagnosis value is larger than the threshold. That is, making an NG judgment on an able-bodied person means making a wrong judgment, whereas making an OK judgment on an able-bodied person means making a correct judgment. In addition, making an NG judgment on a disable-bodied person means making a correct judgment, whereas making an OK judgment on a disable-bodied person means making a wrong judgment. Referring to FIG. 11, the threshold for diagnosis values was 10. In this case, OK judgments were made on 42 able-bodied persons, and NG judgments were made on 14 able-bodied persons. That is, the ability of correctly making OK judgments on able-bodied persons is equivalent to 75%. OK judgments were made on six disable-bodied persons, and NG judgments were made on 29 disable-bodied persons. That is, the ability of correctly making NG judgments on disable-bodied persons is equivalent to 83%.

When the threshold for diagnosis values was 15, the ability of correctly making OK judgments on able-bodied persons was equivalent to 66%, and the ability of correctly making NG judgments on disable-bodied persons was equivalent to 87%.

The ultrasonic diagnosis apparatus 2 according to the second embodiment generates a multivariate state space in the MT system in advance based on the measured values of liver measurement items for the evaluation of a liver disease. At the time of diagnosis, the ultrasonic diagnosis apparatus 2 scans the liver region of the patient with ultrasonic waves, and calculates the measured values of the liver measurement items. The ultrasonic diagnosis apparatus 2 then calculates the Mahalanobis distance of the patient in the state space generated in advance. The ultrasonic diagnosis apparatus 2 compares the Mahalanobis distance with a threshold to automatically determine whether the patient has a liver disease. The second embodiment can therefore provide the ultrasonic diagnosis apparatus 2 and automatic support method which can improve diagnosis efficiency.

Note that this embodiment need not implement the liver disease presence/absence determination function, the liver disease discrimination function, and the like in the ultrasonic diagnosis apparatus 2. For example, as shown in FIG. 7, the embodiment may be an automatic support apparatus (CAD) 90 including the state space database 58, input unit 60, second MD calculation unit 72, disease presence/absence determination unit 74, disease type discrimination unit 76, display control unit 78, and display unit 80. The automatic support apparatus 90 is connected to the ultrasonic diagnosis apparatus including the ultrasonic probe 62, transmission/reception unit 64, B-mode processing unit 66, ultrasonic image generating unit 68, and measured value calculation unit 70 via a network or the like. The automatic support apparatus 90 receives the data of measured values associated with a patient from the measured value calculation unit 70, and stores the data in the internal memory of the second MD calculation unit 72. In response to a start request from a user, the automatic support apparatus 90 calculates the Mahalanobis distance of the patient based on measured values and a state space, and automatically determines by using the calculated Mahalanobis distance whether the patient has a liver disease.

Third Embodiment

An ultrasonic diagnosis apparatus, automatic support apparatus, and automatic support method according to the third embodiment aim at automatically determining whether a subject (fetus) to be diagnosed has Down's syndrome (trisomy 21 syndrome), by applying an MT system to tissue information associated with the cervical region.

FIG. 12 is a block diagram showing the arrangement of an ultrasonic diagnosis apparatus 3 according to the third embodiment. As shown in FIG. 12, the ultrasonic diagnosis apparatus 3 includes an able-bodied person database 100, a disable-bodied person database 102, a state space generating unit 104, and a state space database 106 which are used for offline analysis.

The able-bodied person database 100 stores measured values of Down's syndrome measurement items associated with able-bodied persons. The measured values of the Down's syndrome measurement items are typically measured based on cervical regions of ultrasonic images of able-bodied persons. For example, as a Down's syndrome measurement item, the nuchal translucency (NT value) of the cervical region is used. It is also possible to use, as Down's syndrome measurement items, an examination item associated with maternal blood serum screening and an examination item associated with amniocentesis. The automatic analyzer supplies the measured values of these examination items. Note that an able-bodied person is an infant or fetus determined by a doctor to "have no Down's syndrome" at the time of the acquisition of measured values. That is, each able-bodied person belongs to a unit space.

Like the able-bodied person database 100, the disable-bodied person database 102 stores measured values of Down's syndrome measurement items associated with disable-bodied persons. A disable-bodied person is an infant or fetus determined by a doctor to "have Down's syndrome" at the time of the acquisition of measured values. That is, each disable-bodied person does not belong to a unit space.

The state space generating unit 104 generates a multivariate state space based on measured values of Down's syndrome measurement items stored in the able-bodied person database 100. More specifically, the state space generating unit 104 includes a first MD calculation unit 1042 and a threshold setting unit 1044. The first MD calculation unit 1042 calculates an inverse matrix $R^{-1}$ based on measured values of Down's syndrome measurement items associated with able-bodied persons in accordance with a procedure similar to that in the first embodiment. The first MD calculation unit 1042 then calculates the Mahalanobis distances of the respective able-bodied persons based on measured values of Down's syndrome measurement items. The first MD calculation unit 1042 also calculates the Mahalanobis distances of the respective disable-bodied persons based on measured values of Down's syndrome measurement items. The threshold setting unit 1044 sets a threshold to the Mahalanobis distance located at the boundary between the Mahalanobis distances of the able-bodied persons and the Mahalanobis distances of the disable-bodied persons. Note that it is possible to use only NT values for the generation of a state space.

The state space database 106 stores the state space generated based on the measured values of able-bodied persons.

As shown in FIG. 12, the ultrasonic diagnosis apparatus 3 includes an input unit 108, an ultrasonic probe 110, a transmission/reception unit 112, a B-mode processing unit 114, an ultrasonic image generating unit 116, a measured value calculation unit 118, a second MD calculation unit 120, a disease presence/absence determination unit 122, a display control unit 124, and a display unit 126 which are used for offline analysis.

The input unit 108 receives the measured value data of the Down's syndrome measurement items measured by the automatic analyzer. These measured values include the measured values of the examination items associated with the above maternal blood serum screening and amniocentesis. The input unit 108 supplies the input measured value data to the second MD calculation unit 120.

The transmission/reception unit 112 scans a scanning region including the cervical region of the fetus with ultrasonic waves via the ultrasonic probe 110.

The B-mode processing unit 114 performs B-mode processing for a reception signal from the transmission/reception unit 112, and generates a B-mode signal whose signal strength is expressed by a luminance level. More specifically, the B-mode processing unit 114 performs envelope detection and logarithmic transformation for the reception signal. The generated B-mode signal is supplied to the ultrasonic image generating unit 116.

The ultrasonic image generating unit 116 generates the data of an ultrasonic image of the fetus based on the B-mode signal from the B-mode processing unit 114. The generated ultrasonic image is included in the cervical region. The generated ultrasonic image data is supplied to the measured value calculation unit 118.

The measured value calculation unit 118 calculates the measured values of the Down's syndrome measurement items associated with the fetus based on the cervical region of the ultrasonic image from the ultrasonic image generating unit 116.

The second MD calculation unit 120 calculates the Mahalanobis distance of the fetus in the state space stored in the state space database 106. In this case, the second MD calculation unit 120 may calculate a Mahalanobis distance in consideration of measured values from the automatic analyzer which are input via the input unit 108.

The disease presence/absence determination unit 122 compares the Mahalanobis distance of the fetus with the threshold set by the threshold setting unit 1044 to determine whether the fetus has Down's syndrome.

The display control unit 124 displays the Mahalanobis distance of the fetus and the determination result indicating the presence/absence of Down's syndrome on the display unit 126.

Figure 13:
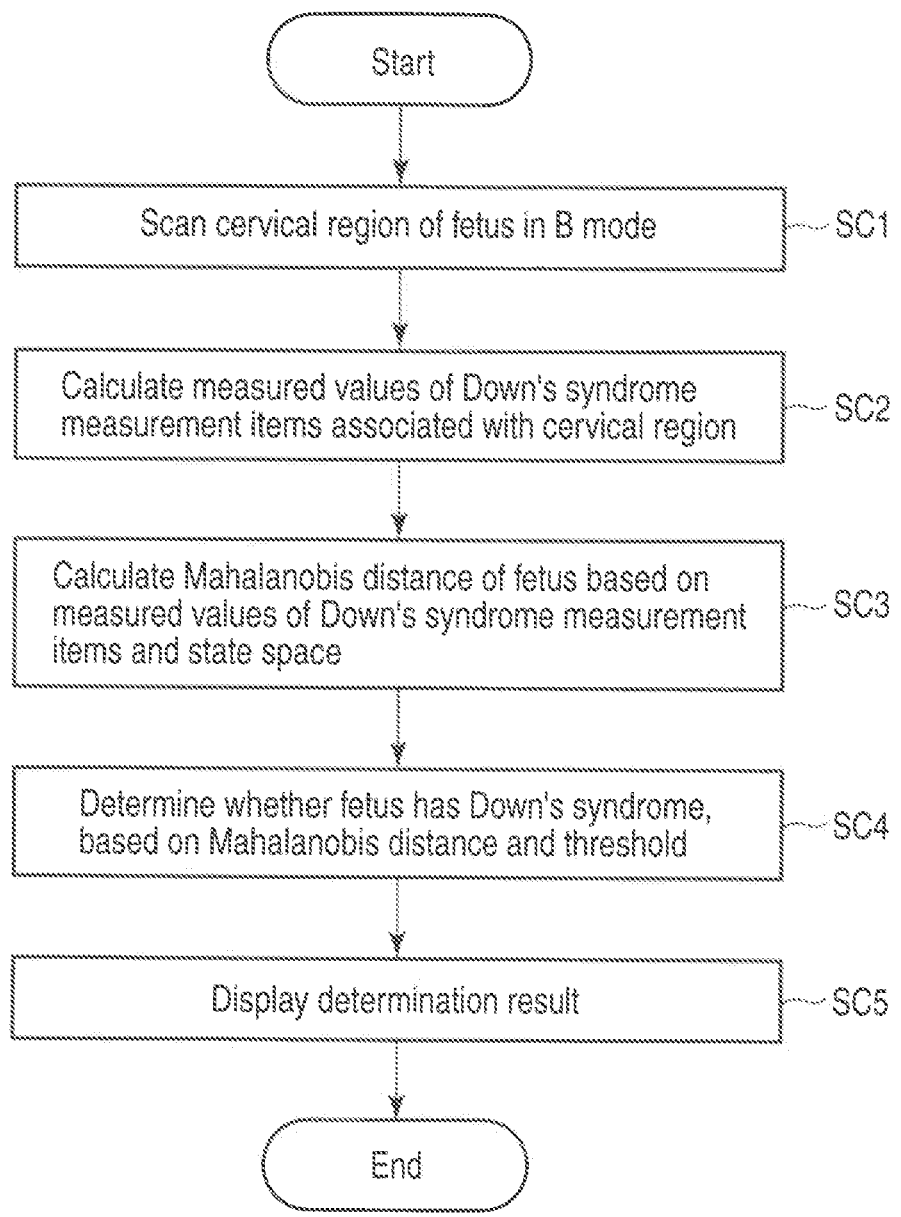
FIG. 13 is a flowchart showing a typical procedure for the processing of automatically determining the presence/absence of Down's syndrome in an infant, which is implemented by the ultrasonic diagnosis apparatus in FIG. 12.

The following is a description of the processing of automatically determining the presence/absence of Down's syndrome in a fetus, which is implemented by the ultrasonic diagnosis apparatus 3. FIG. 13 is a flowchart showing a typical procedure for the processing of automatically determining the presence/absence of Down's syndrome in a fetus. As shown in FIG. 13, first of all, the transmission/reception unit 112 repeatedly scans the cervical region of the fetus in the B mode via the ultrasonic probe 110 (step SC1). In this case, scanning a specific region of the abdominal region of the mother's body can scan the cervical periphery of the fetus. Typically, the presence/absence of Down's syndrome may be tested in the perinatal period of the mother. During B-mode scanning, the B-mode processing unit 114 generates a B-mode signal by performing B-mode processing for the reception signals acquired via the ultrasonic probe 110. The ultrasonic image generating unit 116 generates the data of an ultrasonic image of the fetus based on the generated B-mode signal.

When an ultrasonic image is generated, the measured value calculation unit 118 calculates the measured value of the Down's syndrome measurement item, i.e., an NT value, based on an ultrasonic image (step SC2). The NT value calculated by the measured value calculation unit 118 will be described below.

Figure 14:
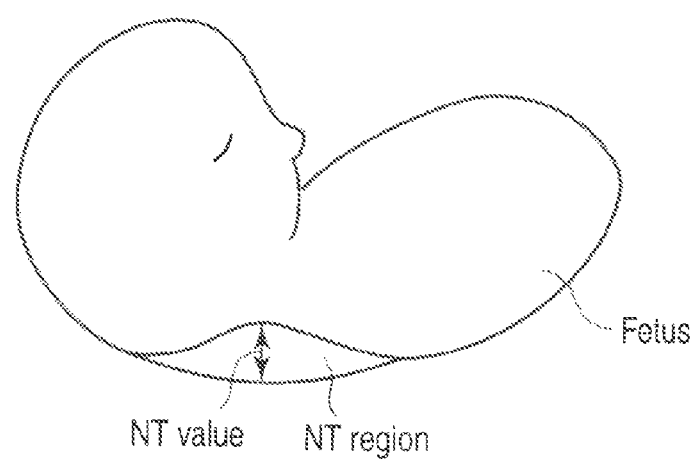
FIG. 14 is a view for explaining the NT value calculated by a measured value calculation unit in FIG. 12.

FIG. 14 is a view for explaining an NT value. As shown in FIG. 14, an NT is an anechoic region existing in the cervical region of a fetus region. An NT value is defined by the thickness of the NT. It is known that an NT value has a strong correlation with Down's syndrome. It is said that the thicker an NT (the larger the NT value), the higher the probability that the chromosome 21 is abnormal. An NT value is measured on a saggital plane. More specifically, the measured value calculation unit 118 specifies an NT region based on luminance values. The measured value calculation unit 118 calculates the maximum inner diameter of the specified NT region as an NT value.

When an NT value is calculated in the above manner, the second MD calculation unit 120 calculates the Mahalanobis distance of a fetus (step SC3). More specifically, the second MD calculation unit 120 calculates the Mahalanobis distance of the fetus based on the measured value of the Down's syndrome measurement item and the state space associated with able-bodied persons. The state space generating unit 104 generates this state space associated with the able-bodied persons in advance before B-mode scanning on the fetus. Note that the second MD calculation unit 120 may calculate a Mahalanobis distance by using the measured values of the measurement items associated with maternal blood serum screening and amniocentesis from the input unit 108.

When the Mahalanobis distance of the fetus is calculated, the disease presence/absence determination unit 122 compares the Mahalanobis distance calculated in step SC3 with a preset threshold to determine whether the fetus has Down's syndrome (step SC4). The state space generating unit 104 generates this threshold in advance before B-mode scanning on the fetus. If the Mahalanobis distance of the fetus is larger than the threshold, the disease presence/absence determination unit 122 determines that the fetus has Down's syndrome. If the Mahalanobis distance of the fetus is smaller than the threshold, the disease presence/absence determination unit 122 determines that the fetus has no Down's syndrome.

When the disease presence/absence determination unit 122 has determined the presence/absence of Down's syndrome, the display control unit 124 displays the determination result obtained in step SC4 on the display unit 126 (step SC5).

With the above operation, this apparatus terminates the processing of automatically determining the presence/absence of Down's syndrome in the fetus.

The ultrasonic diagnosis apparatus 3 according to the third embodiment generates a multivariate state space in the MT system in advance based on the measured values of the Down's syndrome measurement items for the evaluation of Down's syndrome. At the time of diagnosis, the ultrasonic diagnosis apparatus 3 scans the fetus with ultrasonic waves and calculates the measured values of the Down's syndrome measurement items. The ultrasonic diagnosis apparatus 3 then calculates the Mahalanobis distance of the fetus in a state space generated in advance. The ultrasonic diagnosis apparatus 3 compares the Mahalanobis distance with a threshold to automatically determine whether the fetus has Down's syndrome. In this manner, the third embodiment can provide the ultrasonic diagnosis apparatus 3 and automatic support method which improve diagnosis efficiency.

Note that this embodiment need not implement the Down's syndrome presence/absence determination function in the ultrasonic diagnosis apparatus 3. For example, as shown in FIG. 12, the embodiment may be an automatic support apparatus (CAD) 130 including the state space database 106, input unit 108, second MD calculation unit 120, disease presence/absence determination unit 122, display control unit 124, and display unit 126. The automatic support apparatus 130 is connected to the ultrasonic diagnosis apparatus including the ultrasonic probe 110, transmission/reception unit 112, B-mode processing unit 114, ultrasonic image generating unit 116, and measured value calculation unit 118 via a network or the like. The automatic support apparatus 130 receives the data of measured values associated with a fetus from the measured value calculation unit 118, and stores the data in, for example, the internal memory of the second MD calculation unit 72. In response to a start request from the user, the automatic support apparatus 90 calculates the Mahalanobis distance of a patient based on measured values and a state space and automatically determines by using the calculated Mahalanobis distance whether the fetus has Down's syndrome.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnosis apparatus, comprising:
   a storage unit configured to store data of a state space based on a first measured value of a measurement item associated with an able-bodied person;
   an ultrasonic probe;
   a transmission/reception unit configured to transmit an ultrasonic wave to a subject via the ultrasonic probe, receive an ultrasonic wave reflected by the subject, and generate a reception signal corresponding to the received ultrasonic wave;

a measured value calculation unit configured to calculate a second measured value of the measurement item associated with the subject based on the reception signal;
a distance calculation unit configured to calculate a Mahalanobis distance of the subject based on the state space and the second measured value;
a determination unit configured to compare the Mahalanobis distance with a threshold to determine whether the subject has a disease evaluated by the measurement item; and
a disease type discrimination unit configured to discriminate a type of the disease by calculating a similarity between a distribution of second measured values of the subject measured by the measured value calculation unit and a measured value distribution model for each of a plurality of types of diseases.

2. The apparatus according to claim 1, wherein the measurement item is a cardiac measurement item including at least one of a measurement item based on automatic Doppler measurement and a measurement item based on differential/integral analysis on a Doppler trace waveform.

3. The apparatus according to claim 2, further comprising a Doppler processing unit configured to generate a Doppler signal originating from a blood flow in the subject based on the reception signal, wherein
the measured value calculation unit calculates the second measured value of the cardiac measurement item based on the generated Doppler signal,
the distance calculation unit calculates the Mahalanobis distance of the subject based on the state space and the second measured value of the cardiac measurement item, and
the determination unit compares the Mahalanobis distance with the threshold to determine whether the subject has a cardiac disease.

4. The apparatus according to claim 3, wherein the state space is generated based on the first measured value and a waveform feature amount of an electrocardiographic complex associated with the able-bodied person,
the distance calculation unit calculates the Mahalanobis distance of the subject based on the state space, the second measured value, and the waveform feature amount of the electrocardiographic complex associated with the subject, and
the determination unit compares the Mahalanobis distance with a threshold to determine whether the subject has a cardiac disease.

5. The apparatus according to claim 1, wherein the measurement item is a liver measurement item including an image feature amount of a liver region included in an ultrasonic image.

6. The apparatus according to claim 5, which further comprises an image generating unit configured to generate data of an ultrasonic image associated with the liver of the subject based on the reception signal, and in which
the measured value calculation unit calculates a second measured value of the liver measurement item based on the ultrasonic image,
the distance calculation unit calculates a Mahalanobis distance of the subject based on the state space and the second measured value of the liver measurement item, and
the determination unit compares the Mahalanobis distance with the threshold to determine whether the subject has a liver disease.

7. The apparatus according to claim 6, wherein the state space is generated based on the first measured value and a measured value obtained by liver function examination based on blood analysis associated with the able-bodied person,
the distance calculation unit calculates a Mahalanobis distance of the subject based on the state space, the second measured value, and the measured value obtained by the liver function examination based on the blood analysis associated with the subject, and
the determination unit compares the Mahalanobis distance with the threshold to determine whether the subject has a liver disease.

8. The apparatus according to claim 1, wherein the measurement item includes a Down's syndrome measurement item associated with an NT of a cervical region on an ultrasonic image.

9. The apparatus according to claim 8, which further comprises an image generating unit configured to generate data of an ultrasonic image associated with the cervical region of the subject based on the reception signal, and in which
the measured value calculation unit calculates a second measured value of the Down's syndrome measurement item based on the cervical region included in the ultrasonic image,
the distance calculation unit calculates a Mahalanobis distance of the subject based on the state space and the second measured value of the Down's syndrome measurement item, and
the determination unit compares the Mahalanobis distance with the threshold to determine whether the subject has Down's syndrome.

10. The apparatus according to claim 9, wherein the state space is generated based on at least one of the first measured value, a measured value obtained by amniocentesis associated with the able-bodied person, and a measured value obtained by maternal blood serum screening associated with the able-bodied person,
the distance calculation unit calculates a Mahalanobis distance of the subject based on at least one the state space, the second measured value, the measured value obtained by amniocentesis associated with the subject, and the measured value obtained by maternal blood serum screening associated with the subject, and
the determination unit compares the Mahalanobis distance with the threshold to determine whether the subject has Down's syndrome.

11. The apparatus according to claim 1, further comprising a display configured to display a determination result obtained by the determination unit.

12. The apparatus according to claim 1, further comprising a display configured to display a result of a trend analysis.

13. The apparatus according to claim 1, wherein the threshold is set to a Mahalanobis distance located at a boundary between a Mahalanobis distance of the able-bodied person and a Mahalanobis distance of a disable-bodied person.

14. An automatic support apparatus, comprising:
a first storage unit configured to store data of a state space based on a first measured value of a measurement item associated with an able-bodied person;
a second storage unit configured to store data of a second measured value of the measurement item associated with a subject;
a distance calculation unit configured to calculate a Mahalanobis distance of the subject based on the state space and the second measured value;
a determination unit configured to compare the Mahalanobis distance with a threshold to determine whether the subject has a disease evaluated by the measurement item; and a disease type discrimination unit configured to discriminate a type of the disease by calculating a similarity between a distribution of second measured values of the subject and a measured value distribution model for each of a plurality of types of diseases.

15. An automatic support method, comprising:

scanning a subject with an ultrasonic wave via an ultrasonic probe;

calculating a measured value of an ultrasonic measurement item associated with the subject based on a reception signal from the ultrasonic probe;

calculating a Mahalanobis distance of the subject based on the calculated measured value and a state space based on the measured value of the measurement item associated with an able-bodied person;

comparing the calculated Mahalanobis distance with a threshold to determine whether the subject has a disease evaluated by the measurement item; and discriminating a type of the disease by calculating a similarity between a distribution of measured values of the subject and a measured value distribution model for each of a plurality of types of diseases.

* * * * *